(12) United States Patent
Varki et al.

(10) Patent No.: US 8,232,448 B2
(45) Date of Patent: Jul. 31, 2012

(54) TRANSGENIC MOUSE WITH A HOMOZYGOUS MUTATION IN THE CMAH GENE

(75) Inventors: Ajit Varki, La Jolla, CA (US); Anna Maria Hedlund, San Diego, CA (US); Dzung Nguyen, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 352 days.

(21) Appl. No.: 12/600,378

(22) PCT Filed: Jun. 8, 2006

(86) PCT No.: PCT/US2006/022282
§ 371 (c)(1),
(2), (4) Date: Nov. 16, 2009

(87) PCT Pub. No.: WO2006/133356
PCT Pub. Date: Dec. 14, 2006

(65) Prior Publication Data
US 2010/0293624 A1    Nov. 18, 2010

Related U.S. Application Data

(60) Provisional application No. 60/688,867, filed on Jun. 8, 2005.

(51) Int. Cl.
*A01K 67/027* (2006.01)
*C12N 15/00* (2006.01)
*C12N 15/87* (2006.01)
(52) U.S. Cl. ............. 800/18; 800/22; 435/462; 435/463
(58) Field of Classification Search .............. 800/18, 800/22; 435/462, 463
See application file for complete search history.

(56) References Cited

U.S. PATENT DOCUMENTS

| | | | |
|---|---|---|---|
| 6,300,129 B1 | 10/2001 | Lonberg et al. | |
| 6,852,533 B1 | 2/2005 | Rafil et al. | |
| 6,872,868 B1 | 3/2005 | Wagner et al. | |
| 2007/0089178 A1 | 4/2007 | Zhu | |
| 2008/0166805 A1 | 7/2008 | Varki et al. | |

FOREIGN PATENT DOCUMENTS
WO    2005/033303 A1    4/2005

OTHER PUBLICATIONS

Clark et al. Nature Reviews: Genetics. 2003, 825-833.*
Niemann et al. Rev. Sci, Tech. Off. Int. Spiz. 2005, (24), 285-298.*
Wheeler. Theriogenology. 2001, (56), 1345-1369.*
Prelle. Anat. Histol. Embryol. 2002, vol. 31, 169-186.*
Smith. Journal of Biotechnology, 99:1-22, 2002.*
Denning and Priddle. Reproduction, 126:1-11. 2003.*
Mullins et al. J. Clin. Invest. 97:1557-1560 (1996).*
Cao et al. J. of Exp. Zoo., 311A: 368-376, 2009.*
Brevini et al. Theriogenology, 74: 544-550, 2010.*
Paris et al. Theriogenology, 74: 516-524, 2010.*
Wright et al. ILAR Journal, 45(3): 314-323, 2004.*
Taniguichi et al. Genome Biology, 7: R116.1-R116.14, 2006.*
Capecchi. Scientific American, 1994, 270:34-41.*
Kawano et al. JBC, 270(27): 16458-16463, 1995.*
Thomson et al. Reprod. Supp., 61:495-508, 2003.*
Westhusin et al. Theriogenology, vol. 55, pp. 35-49, 2001.*
Lee et al. Nature, 436: 641, 2005.*
Mullins et al. J. Physiol, 554.1, pp. 4-12, 2003.*
Jiang. J. of Reprod. and Development, 48(5): 505-511, 2002.*
Swiss Institute of Bioinformatics. www.expasy.org/uniprot/Q6GML1 (Sequene last modified on Nov. 1, 1996, integrated into Swiss-prot May 10, 2005).
Martin et al., Abstract #4182, Blood, (Nov. 16, 2004) vol. 104, No. 11, Part 2, pp. 132B. Meeting Info. 46th Annual Meeting of the American-Society-of-Hematology. San Diego, CA, USA. Dec. 4-7, 2004.
Martin et al., Nature Medicine, Feb. 2005, pp., 228-232, vol. 11, No. 2, available on-line Jan. 30, 2005.
Tangvoranuntakul et al., Proc. Natl. Acad. Sci, USA, Oct. 14, 2003, pp. 12045-12050, vol. 100, No. 21.
Amit et al., Dev. Biol. 2000, pp. 271-278, vol. 227.
GIBCO catalog, "Knockout SR", accessed online at www.invitrogen.com on May 8, 2009.
Amit et al., Biol. of Reprod., 2004 (available on-line Nov. 19, 2003), pp. 837-845, vol. 70.
Richards et al., Nature Biotech., 2002, pp. 933-936, vol. 20.

* cited by examiner

Primary Examiner — Thaian N Ton
(74) Attorney, Agent, or Firm — Medlen & Carroll, LLP

(57) ABSTRACT

This application is in the field of sialic acid chemistry, metabolism, antigenicity, and the production of transgenic non-human mammals with altered sialic acid production. More particularly, this application relates to N-glycolylneuraminic acid (Neu5Gc) being an immunogen in humans, and the production of Neu5Gc-free mammalian products for laboratory and human use.

3 Claims, 17 Drawing Sheets

FIGURE 16

```
            10         20         30         40         50         60
    MDENNGLLLL ELNPPNPWDL QPRSPEELAF GEVQITYLTH ACMDLKLGDK RMVFDPWLIG 70         80         90        100        110        120
    PAFARGWWLL HEPPSDWLER LCQADLIYIS HLHSDHLSYP TLKKLAGRRP DIPIYVGNTE
                                    Box 2

130        140        150        160        170        180
    RPVFWNLNQS GVQLTNINVV PFGIWQQVDK NLRFMILMDG VHPEMDTCII VEYKGHKILN 190        200        210        220        230        240
    IVDCTRPNGG RLPMKVALMM SDFAG GASGF PMTFSGGKFT EEW KAQFIKT ERKKLLNYKA
                                Box 3                Box 4

250        260        270        280        290        300
    RLVK NLQPRI YCPFAGYFVE SHPSDKYIKE TNTKNDPNEL NNLIKKNSDV ITWTPRPGAT
    Box 4 - Continued 310        320        330        340        350        360
    LDLGRMLKDR TDSKGIIEPP EGTKIYKDSW DFEPYLEILN AALGDEIFLH SSWIKEYFTW 370        380        390        400        410        420
    AGFKDYNLVV RMIETDEDFN PFPGGYDYLV DFLDLSFPKE RPQREHPYEE IHSRVDVIRH 430        440        450        460        470        480
    VVKNGLLWDE LYIGFQTRLQ RDPDIY HHLF WNH FQIKLPL TPPNWKSFLM CCEQNGPVIL
                                 Box 5

QECKTT
```

FIGURE 17

SEQUENCE LISTING

```
<160> NUMBER OF SEQ ID NOS: 12

<210> SEQ ID NO 1
<211> LENGTH: 653
<212> TYPE: PRT
<213> ORGANISM: Asterias rubens

<400> SEQUENCE: 1

Met Glu Gln Glu Arg Glu Ile Val Phe Ser Leu Ser Pro Glu Glu Thr
1               5                   10                  15

Ser Glu Leu Lys Asn Gly Val Asn Leu Ile Ser Arg Ser Glu Lys Glu
            20                  25                  30

Lys Phe Val Ile Tyr Lys Asp Pro Thr Ala Glu Asn Thr Val Glu Glu
        35                  40                  45

Pro Ala Thr Ser His Met Tyr Lys Ala Cys Leu Asn Lys Cys Lys His
    50                  55                  60

Gln Gly Gly Thr Phe Ile Lys Asp Ile Glu Asp Gly Asp Asn Cys Ile
65                  70                  75                  80
```

```
Leu Arg Cys Thr Lys His Gly Trp Lys Leu Asp Ala Lys Thr Met Arg
                85                  90                  95

Tyr Val Asn Pro Pro Asp Ser Phe Ser Gln Gln Leu Val Pro Glu
            100                 105                 110

Tyr Asn Glu Asp Gly Ser Leu Asp Ile Val Glu Leu Lys Pro Pro Gln
            115                 120                 125

Pro Trp Glu Thr Asp Lys Arg Asp Pro Met Pro Leu Glu Val Gly Glu
        130                 135                 140

Val Gln Ile Thr Tyr Phe Thr His Ala Cys Ile Glu Ile Lys Leu Gly
145                 150                 155                 160

Asp Leu Ile Met Phe Thr Asp Pro Trp Leu Ile Gly Pro Ala Phe Ala
                165                 170                 175

Arg Gly Trp Trp Leu Met His Glu Pro Pro Ala Asp Trp Leu Asp Arg
            180                 185                 190

Leu Ala Lys Ala Asp Leu Ile Tyr Ile Ser His Leu His Ser Asp His
            195                 200                 205

Leu Asn Tyr Pro Thr Leu Glu Leu Leu Ser Gln Arg Asn Pro Asp Ile
    210                 215                 220

Pro Ile Tyr Val Gly Asp Thr Ser Met Pro Val Phe Val Arg Leu Glu
225                 230                 235                 240

Gln Ser Gly Val Lys Leu Asn Asn Ile His Ile Lys Lys Phe Gly Lys
                245                 250                 255

Trp Ile Glu Ile Asn Lys Asp Thr Arg Phe Met Ile Met Met Asp Gly
            260                 265                 270

Val His Pro Asp Met Asp Thr Cys Ala Leu Ile Asp Tyr Lys Gly His
        275                 280                 285

Leu Ile Leu Asp Thr Val Asp Cys Thr Asn Pro Asn Gly Gly Arg Leu
    290                 295                 300

Pro Ile Gly Val Asp Met Met Leu Ser Asp Phe Ala Gly Gly Ala Ser
305                 310                 315                 320

Gly Phe Pro Met Thr Phe Ser Gly Gly Lys Tyr Thr Glu Glu Trp Lys
                325                 330                 335

Ala Glu Phe Val Lys Arg Glu Arg Arg Lys Leu Leu Tyr Tyr Lys Met
            340                 345                 350

Gln Gln Val Arg Asp Val Ala Pro Thr Val Tyr Cys Pro Phe Ala Gly
        355                 360                 365

Tyr Phe Val Glu Ala His Pro Ser Asp His Tyr Ile Arg Ser Thr Asn
    370                 375                 380

Thr Lys Asn Asp Pro Asp Ala Leu Asn Ala Leu Ile Asn Lys Tyr Ser
385                 390                 395                 400

Pro Asn Ile Lys Thr Trp Ser Pro Ser Pro Gly Ala Val Leu Asp Leu
                405                 410                 415

Lys Lys Ala Ile Gln Gly Asp Arg Asp Phe Ile Thr Asp Pro Pro Arg
            420                 425                 430

Gly Thr Gln Lys Phe Lys Asp Ser Trp Asp Phe Glu Lys Tyr Val Asn
        435                 440                 445

Ala Ile Asn Lys Asn Ile Glu Glu Ile Phe Ser Tyr Pro Glu Trp
    450                 455                 460

Ile Gln Phe Tyr Lys Trp Thr Gly Phe Lys Asn Tyr Asn Leu Val
465                 470                 475                 480

Ile Arg Met Val Glu Arg Asp Asp Phe Cys Pro Val Val Gly Gly
                485                 490                 495

Tyr Asp Phe Met Val Asp Phe Val Gly Glu Pro Thr Phe Pro Thr
            500                 505                 510
```

```
Glu Arg Pro Ala Arg Glu His Ser Tyr Leu Glu Met Glu Asn Arg Ile
            515                 520                 525

Gly Val His Arg Glu Thr Val Arg Gln Gly Leu Phe Trp Asp Asp Leu
        530                 535                 540

Tyr Ile Gly Phe Asn Asn Arg Ile Ser Arg Glu Pro Asp Thr Phe His
545                 550                 555                 560

Tyr Leu Phe Trp Asn His Met Gln Ile Leu Leu Pro Arg Thr Asp Pro
                565                 570                 575

Asp Trp Glu Gly Phe Leu Arg Asp Met Lys Thr Glu Gly Ala Pro Gln
            580                 585                 590

Lys Ala Ile Trp Asn Pro Ser Gln Ala Thr Pro Ala Val Glu Ala Lys
        595                 600                 605

Asp Pro Ser Asp Ser Lys Asp Ser Ala Thr Lys Pro Gly Thr His
610                 615                 620

Trp Asn Tyr Glu Arg Leu Leu Arg Pro Leu Gly Ile Val Val Ala Leu
625                 630                 635                 640

Val Gly Val Gly Val Ala Ile Trp Lys Ser Glu Ser Lys
            645                 650

<210> SEQ ID NO 2
<211> LENGTH: 577
<212> TYPE: PRT
<213> ORGANISM: Mus musculus

<400> SEQUENCE: 2

Met Met Asp Arg Lys Gln Thr Ala Glu Thr Leu Leu Thr Leu Ser Pro
1               5                   10                  15

Ala Glu Val Ala Asn Leu Lys Glu Gly Ile Asn Phe Phe Arg Asn Lys
            20                  25                  30

Thr Thr Gly Lys Glu Tyr Ile Leu Tyr Lys Glu Lys Asp His Leu Lys
        35                  40                  45

Ala Cys Lys Asn Leu Cys Lys His Gln Gly Gly Leu Phe Met Lys Asp
    50                  55                  60

Ile Glu Asp Leu Asp Gly Arg Ser Val Lys Cys Thr Lys His Asn Trp
65                  70                  75                  80

Lys Leu Asp Val Ser Thr Met Lys Tyr Ile Asn Pro Pro Gly Ser Phe
                85                  90                  95

Cys Gln Asp Glu Leu Val Ile Glu Met Asp Glu Asn Asn Gly Leu Ser
            100                 105                 110

Leu Val Glu Leu Asn Pro Pro Asn Pro Trp Asp Ser Asp Pro Arg Ser
        115                 120                 125

Pro Glu Glu Leu Ala Phe Gly Glu Val Gln Ile Thr Tyr Leu Thr His
    130                 135                 140

Ala Cys Met Asp Leu Lys Leu Gly Asp Lys Arg Met Val Phe Asp Pro
145                 150                 155                 160

Trp Leu Ile Gly Pro Ala Phe Ala Arg Gly Trp Trp Leu Leu His Glu
                165                 170                 175

Pro Pro Ser Asp Trp Leu Glu Arg Leu Cys Lys Ala Asp Leu Ile Tyr
            180                 185                 190

Ile Ser His Met His Ser Asp His Leu Ser Tyr Pro Thr Leu Lys Gln
        195                 200                 205

Leu Ser Gln Arg Arg Pro Asp Ile Pro Ile Tyr Val Gly Asp Thr Glu
    210                 215                 220

Arg Pro Val Phe Trp Asn Leu Asp Gln Ser Gly Val Gly Leu Thr Asn
225                 230                 235                 240
```

Ile Asn Val Val Pro Phe Gly Ile Trp Gln Gln Val Asp Lys Ser Leu
            245                 250                 255

Arg Phe Met Ile Leu Met Asp Gly Val His Pro Glu Met Asp Thr Cys
            260                 265                 270

Ile Ile Val Glu Tyr Lys Gly His Lys Ile Leu Asn Thr Val Asp Cys
            275                 280                 285

Thr Arg Pro Asn Gly Gly Arg Leu Pro Glu Lys Val Ala Leu Met Met
        290                 295                 300

Ser Asp Phe Ala Gly Gly Ala Ser Gly Phe Pro Met Thr Phe Ser Gly
305                 310                 315                 320

Gly Lys Phe Thr Glu Glu Trp Lys Ala Gln Phe Ile Lys Ala Glu Arg
            325                 330                 335

Arg Lys Leu Leu Asn Tyr Lys Ala Gln Leu Val Lys Asp Leu Gln Pro
            340                 345                 350

Arg Ile Tyr Cys Pro Phe Ala Gly Tyr Phe Val Glu Ser His Pro Ser
            355                 360                 365

Asp Lys Tyr Ile Lys Glu Thr Asn Thr Lys Asn Asp Pro Asn Gln Leu
        370                 375                 380

Asn Asn Leu Ile Arg Lys Asn Ser Asp Val Val Thr Trp Thr Pro Arg
385                 390                 395                 400

Pro Gly Ala Val Leu Asp Leu Gly Arg Met Leu Lys Asp Pro Thr Asp
            405                 410                 415

Ser Lys Gly Ile Val Glu Pro Pro Glu Gly Thr Lys Ile Tyr Lys Asp
            420                 425                 430

Ser Trp Asp Phe Gly Pro Tyr Leu Glu Ile Leu Asn Ser Ala Val Arg
        435                 440                 445

Asp Glu Ile Phe Cys His Ser Ser Trp Ile Lys Glu Tyr Phe Thr Trp
    450                 455                 460

Ala Gly Phe Lys Asn Tyr Asn Leu Val Val Arg Met Ile Glu Thr Asp
465                 470                 475                 480

Glu Asp Phe Ser Pro Phe Pro Gly Gly Tyr Asp Tyr Leu Val Asp Phe
            485                 490                 495

Leu Asp Leu Ser Phe Pro Lys Glu Arg Pro Ser Arg Glu His Pro Tyr
            500                 505                 510

Glu Glu Ile His Ser Arg Val Asp Val Ile Arg Tyr Val Val Lys Asn
            515                 520                 525

Gly Leu Leu Trp Asp Asp Leu Tyr Ile Gly Phe Gln Thr Arg Leu Leu
530                 535                 540

Arg Asp Pro Asp Ile Tyr His His Leu Phe Trp Asn His Phe Gln Ile
545                 550                 555                 560

Lys Leu Pro Leu Thr Pro Pro Asn Trp Lys Ser Phe Leu Met His Cys
            565                 570                 575

Asp

<210> SEQ ID NO 3
<211> LENGTH: 563
<212> TYPE: PRT
<213> ORGANISM: Cricetulus griseus

<400> SEQUENCE: 3

Lys Gln Thr Ala Glu Thr Leu Leu Ser Leu Ser Pro Ala Glu Thr Ala
1               5                   10                  15

Asn Leu Lys Glu Gly Ile Asn Phe Phe Arg Asn Lys Thr Thr Gly Lys
            20                  25                  30

-continued

```
Glu Tyr Ile Leu Tyr Lys Glu Lys Asn His Leu Lys Ala Cys Lys Asn
             35                  40                  45
Leu Cys Lys His Gln Gly Gly Leu Phe Ile Lys Asp Ile Glu Asp Leu
 50                  55                  60
Asp Gly Arg Ser Val Lys Cys Thr Lys His Asn Trp Lys Leu Asp Val
 65                  70                  75                  80
Ser Thr Met Lys Tyr Ile Asn Pro Pro Gly Ser Phe Cys Gln Asp Glu
                 85                  90                  95
Leu Val Val Glu Met Asp Gly Asn Asp Gly Leu Phe Leu Ile Glu Leu
                100                 105                 110
Asn Pro Pro Asn Pro Trp Asp Ser Asp Pro Arg Thr Pro Glu Glu Leu
            115                 120                 125
Ala Phe Gly Glu Val Gln Ile Thr Tyr Leu Thr His Ala Cys Met Asp
        130                 135                 140
Leu Lys Leu Gly Asp Lys Arg Met Val Phe Asp Pro Trp Leu Ile Gly
145                 150                 155                 160
Pro Ala Phe Ala Arg Gly Trp Trp Leu Leu His Glu Pro Pro Ser Asp
                165                 170                 175
Trp Leu Glu Arg Leu Cys Lys Ala Asp Leu Ile Tyr Ile Ser His Met
            180                 185                 190
His Ser Asp His Leu Ser Tyr Pro Thr Leu Lys Gln Leu Ser Gln Arg
        195                 200                 205
Arg Pro Asp Ile Pro Ile Tyr Val Gly Asp Thr Glu Arg Pro Val Phe
    210                 215                 220
Trp Asn Leu Asp Gln Ser Gly Val Gln Leu Thr Asn Ile Asn Val Val
225                 230                 235                 240
Pro Phe Gly Val Trp Gln Gln Val Asp Lys Asn Leu Arg Phe Met Ile
                245                 250                 255
Leu Met Asp Gly Val His Pro Glu Met Asp Thr Cys Ile Ile Val Glu
            260                 265                 270
Tyr Lys Gly His Lys Ile Leu Asn Thr Val Asp Cys Thr Arg Pro Asn
        275                 280                 285
Gly Gly Arg Leu Pro Glu Lys Ala Ala Leu Met Met Ser Asp Phe Ala
    290                 295                 300
Gly Gly Ala Ser Gly Phe Pro Met Thr Phe Ser Gly Gly Lys Phe Thr
305                 310                 315                 320
Glu Glu Trp Lys Ala Gln Phe Ile Lys Ala Glu Arg Arg Lys Leu Leu
                325                 330                 335
Asn Tyr Lys Ala Gln Leu Val Lys Asp Leu Gln Pro Arg Ile Tyr Cys
            340                 345                 350
Pro Phe Ala Gly Tyr Phe Val Glu Ser His Pro Ser Asp Lys Tyr Ile
        355                 360                 365
Lys Glu Thr Asn Ile Lys Asn Asp Pro Ile Gln Leu Asn Asn Leu Ile
    370                 375                 380
Lys Lys Asn Cys Asp Val Val Thr Trp Thr Pro Arg Pro Gly Ala Thr
385                 390                 395                 400
Leu Asp Leu Gly Arg Met Leu Lys Asp Pro Thr Asp Ser Gln Gly Ile
                405                 410                 415
Ile Glu Pro Pro Glu Gly Thr Lys Ile Tyr Lys Asp Ser Trp Asp Phe
            420                 425                 430
Gly Pro Tyr Leu Ser Thr Leu His Ser Ala Val Gly Asp Glu Ile Phe
        435                 440                 445
Leu His Ser Ser Trp Ile Lys Glu Tyr Phe Thr Trp Ala Gly Phe Lys
    450                 455                 460
```

```
Ser Tyr Asn Leu Val Val Arg Met Ile Glu Thr Asp Glu Asp Phe Asn
465                 470                 475                 480

Pro Phe Pro Gly Gly Tyr Asp Tyr Leu Val Asp Phe Leu Asp Leu Ser
            485                 490                 495

Phe Pro Lys Glu Arg Pro Ser Arg Glu His Pro Tyr Glu Glu Ile Arg
            500                 505                 510

Ser Arg Val Asp Val Val Arg Tyr Val Lys His Gly Leu Leu Trp
            515                 520                 525

Asp Asp Leu Tyr Ile Gly Phe Gln Thr Arg Leu Gln Arg Asp Pro Asp
            530                 535                 540

Ile Tyr His His Leu Phe Trp Asn His Phe Gln Ile Lys Leu Pro Leu
545                 550                 555                 560

Thr Pro Pro

<210> SEQ ID NO 4
<211> LENGTH: 435
<212> TYPE: PRT
<213> ORGANISM: Sus scrofa

<400> SEQUENCE: 4

Thr His Ala Cys Met Asp Leu Lys Leu Gly Asp Lys Arg Met Val Phe
1               5                   10                  15

Asp Pro Trp Leu Ile Gly Pro Ala Phe Ala Arg Gly Trp Trp Leu Leu
            20                  25                  30

His Glu Pro Pro Ser Asp Trp Leu Glu Arg Leu Ser Arg Ala Asp Leu
            35                  40                  45

Ile Tyr Ile Ser His Met His Ser Asp His Leu Ser Tyr Pro Thr Leu
50                  55                  60

Lys Lys Leu Ala Glu Arg Arg Pro Asp Val Pro Ile Tyr Val Gly Asn
65                  70                  75                  80

Thr Glu Arg Pro Val Phe Trp Asn Leu Asn Gln Ser Val Gln Leu
                85                  90                  95

Thr Asn Ile Asn Val Val Pro Phe Gly Ile Trp Gln Gln Val Asp Lys
            100                 105                 110

Asn Leu Arg Phe Met Ile Leu Met Asp Gly Val His Pro Glu Met Asp
            115                 120                 125

Thr Cys Ile Ile Val Glu Tyr Lys Gly His Lys Ile Leu Asn Thr Val
            130                 135                 140

Asp Cys Thr Arg Pro Asn Gly Gly Arg Leu Pro Met Lys Val Ala Leu
145                 150                 155                 160

Met Met Ser Asp Phe Ala Gly Gly Ala Ser Gly Phe Pro Met Thr Phe
                165                 170                 175

Ser Gly Gly Lys Phe Thr Glu Glu Trp Lys Ala Gln Phe Ile Lys Thr
            180                 185                 190

Glu Arg Lys Lys Leu Leu Asn Tyr Lys Ala Arg Leu Val Lys Asp Leu
            195                 200                 205

Gln Pro Arg Ile Tyr Cys Pro Phe Pro Gly Tyr Phe Val Glu Ser His
            210                 215                 220

Pro Ala Asp Lys Tyr Ile Lys Glu Thr Asn Ile Lys Asn Asp Pro Asn
225                 230                 235                 240

Glu Leu Asn Asn Leu Ile Lys Lys Asn Ser Glu Val Val Thr Trp Thr
                245                 250                 255

Pro Arg Pro Gly Ala Thr Leu Asp Leu Gly Arg Met Leu Lys Asp Pro
            260                 265                 270
```

```
Thr Asp Ser Lys Gly Ile Val Glu Pro Pro Glu Gly Thr Lys Ile Tyr
        275                 280                 285

Lys Asp Ser Trp Asp Phe Gly Pro Tyr Leu Asn Ile Leu Asn Ala Ala
290                 295                 300

Ile Gly Asp Glu Ile Phe Arg His Ser Ser Trp Ile Lys Glu Tyr Phe
305                 310                 315                 320

Thr Trp Ala Gly Phe Lys Asp Tyr Asn Leu Val Val Arg Met Ile Glu
                325                 330                 335

Thr Asp Glu Asp Phe Ser Pro Leu Pro Gly Gly Tyr Asp Tyr Leu Val
            340                 345                 350

Asp Phe Leu Asp Leu Ser Phe Pro Lys Glu Arg Pro Ser Arg Glu His
            355                 360                 365

Pro Tyr Glu Glu Ile Arg Ser Arg Val Asp Val Ile Arg His Val Val
370                 375                 380

Lys Asn Gly Leu Leu Trp Asp Asp Leu Tyr Ile Gly Phe Gln Thr Arg
385                 390                 395                 400

Leu Gln Arg Asp Pro Asp Ile Tyr His His Leu Phe Trp Asn His Phe
                405                 410                 415

Gln Ile Lys Leu Pro Leu Thr Pro Pro Asp Trp Lys Ser Phe Leu Met
            420                 425                 430

Cys Ser Gly
        435

<210> SEQ ID NO 5
<211> LENGTH: 590
<212> TYPE: PRT
<213> ORGANISM: Pan troglodytes

<400> SEQUENCE: 5

Met Gly Ser Ile Glu Gln Thr Thr Glu Ile Leu Leu Cys Leu Ser Pro
1               5                   10                  15

Val Glu Val Ala Ser Leu Lys Glu Gly Ile Asn Phe Phe Arg Asn Lys
                20                  25                  30

Ser Thr Gly Lys Asp Tyr Ile Leu Tyr Lys Asn Lys Ser Arg Leu Arg
            35                  40                  45

Ala Cys Lys Asn Met Cys Lys His Gln Gly Gly Leu Phe Ile Lys Asp
50                  55                  60

Ile Glu Asp Leu Ala Gly Arg Ser Val Arg Cys Thr Lys His Asn Trp
65                  70                  75                  80

Lys Leu Asp Val Ser Thr Met Lys Tyr Ile Asn Pro Pro Glu Ser Phe
                85                  90                  95

Cys Gln Asp Glu Leu Val Val Glu Met Asp Glu Asn Asn Arg Leu Leu
            100                 105                 110

Leu Leu Glu Leu Asn Pro Pro Asn Pro Trp Asp Leu Gln Pro Arg Ser
        115                 120                 125

Pro Glu Glu Leu Ala Phe Gly Glu Val Gln Ile Thr Tyr Leu Thr His
    130                 135                 140

Ala Cys Met Asp Leu Lys Leu Gly Asp Lys Arg Met Val Phe Asp Pro
145                 150                 155                 160

Trp Leu Ile Gly Pro Ala Phe Ala Arg Gly Trp Trp Leu Leu His Glu
                165                 170                 175

Pro Pro Ser Asp Trp Leu Glu Arg Leu Cys Gln Ala Asp Leu Ile Tyr
            180                 185                 190

Ile Ser His Leu His Ser Asp His Leu Ser Tyr Pro Thr Leu Lys Lys
        195                 200                 205
```

Leu Ala Gly Arg Arg Pro Asp Ile Pro Ile Tyr Val Gly Asn Thr Glu
210                 215                 220

Arg Pro Val Phe Trp Asn Leu Asn Gln Ser Gly Val Gln Leu Thr Asn
225                 230                 235                 240

Ile Asn Val Val Pro Phe Gly Ile Trp Gln Gln Val Asp Lys Asn Leu
                245                 250                 255

Arg Phe Met Ile Leu Met Asp Gly Val His Pro Glu Met Asp Thr Cys
            260                 265                 270

Ile Ile Val Glu Tyr Lys Gly His Lys Ile Leu Asn Thr Val Asp Cys
        275                 280                 285

Thr Arg Pro Asn Gly Gly Arg Leu Pro Met Lys Val Ala Leu Met Met
290                 295                 300

Ser Asp Phe Ala Gly Gly Ala Ser Gly Phe Pro Met Thr Phe Ser Gly
305                 310                 315                 320

Gly Lys Phe Thr Glu Glu Trp Lys Ala Gln Phe Ile Lys Thr Glu Arg
                325                 330                 335

Lys Lys Leu Leu Asn Tyr Lys Ala Arg Leu Val Lys Asn Leu Gln Pro
            340                 345                 350

Arg Ile Tyr Cys Pro Phe Ala Gly Tyr Phe Val Glu Ser His Pro Ser
        355                 360                 365

Asp Lys Tyr Ile Lys Glu Thr Asn Thr Lys Asn Asp Pro Asn Glu Leu
370                 375                 380

Asn Asn Leu Ile Lys Lys Asn Ser Asp Val Ile Thr Trp Thr Pro Arg
385                 390                 395                 400

Pro Gly Ala Thr Leu Asp Leu Gly Arg Met Leu Lys Asp Pro Thr Asp
                405                 410                 415

Ser Lys Gly Ile Ile Glu Pro Pro Glu Gly Thr Lys Ile Tyr Lys Asp
            420                 425                 430

Ser Trp Asp Phe Glu Pro Tyr Leu Glu Ile Leu Asn Ala Ala Val Gly
        435                 440                 445

Asp Glu Ile Phe Leu His Ser Ser Trp Ile Lys Glu Tyr Phe Thr Trp
450                 455                 460

Ala Gly Phe Lys Asp Tyr Asn Leu Val Val Arg Met Ile Glu Thr Asp
465                 470                 475                 480

Glu Asp Phe Asn Pro Phe Pro Gly Gly Tyr Asp Tyr Leu Val Asp Phe
                485                 490                 495

Leu Asp Leu Ser Phe Pro Lys Glu Arg Pro Gln Arg Glu His Pro Tyr
            500                 505                 510

Glu Glu Ile His Ser Arg Val Asp Val Ile Arg His Val Val Lys Asn
        515                 520                 525

Gly Leu Leu Trp Asp Glu Leu Tyr Ile Gly Phe Gln Thr Arg Leu Gln
530                 535                 540

Arg Asp Pro Asp Ile Tyr His His Leu Phe Trp Asn His Phe Gln Ile
545                 550                 555                 560

Lys Leu Pro Leu Thr Pro Pro Asn Trp Lys Ser Phe Leu Met Cys Cys
                565                 570                 575

Glu Gln Asn Gly Pro Gly Ile Leu Gln Glu Cys Lys Thr Thr
            580                 585                 590

<210> SEQ ID NO 6
<211> LENGTH: 590
<212> TYPE: PRT
<213> ORGANISM: Macaca mulatta

<400> SEQUENCE: 6

-continued

```
Met Gly Ser Thr Glu Gln Thr Thr Glu Ile Leu Leu Cys Leu Ser Pro
1               5                   10                  15

Val Glu Val Ala Asn Leu Lys Glu Gly Ile Asn Phe Phe Arg Asn Lys
                20                  25                  30

Ser Thr Gly Lys Asp Tyr Ile Leu Tyr Lys Ser Lys Ser Arg Leu Arg
            35                  40                  45

Ala Cys Lys Asn Val Cys Lys His Gln Gly Gly Leu Phe Ile Lys Asp
        50                  55                  60

Ile Glu Asp Leu Ala Gly Arg Ser Val Arg Cys Thr Lys His Asn Trp
65                      70                  75                  80

Lys Leu Asp Val Ser Thr Met Lys Tyr Ile Asn Pro Pro Glu Ser Phe
                    85                  90                  95

Cys Gln Asp Glu Leu Val Val Glu Met Asp Glu Asn Asn Gly Leu Leu
                100                 105                 110

Leu Leu Glu Leu Asn Pro Pro Asn Pro Trp Asp Ser Glu Pro Arg Ser
            115                 120                 125

Pro Glu Glu Leu Asp Phe Gly Glu Val Gln Ile Thr Tyr Leu Thr His
        130                 135                 140

Ala Cys Met Asp Leu Lys Leu Gly Asp Lys Arg Met Val Phe Asp Pro
145                 150                 155                 160

Trp Leu Ile Gly Pro Ala Phe Ala Arg Gly Trp Leu Leu His Glu
                    165                 170                 175

Pro Pro Ser Asp Trp Leu Glu Arg Leu Cys Gln Ala Asp Leu Ile Tyr
                180                 185                 190

Ile Ser His Leu His Ser Asp His Leu Ser Tyr Pro Thr Leu Lys Lys
            195                 200                 205

Leu Ala Gly Arg Arg Pro Asp Ile Pro Ile Tyr Val Gly Asn Thr Glu
210                 215                 220

Arg Pro Val Phe Trp Asn Leu Asn Gln Ser Gly Val Gln Leu Thr Asn
225                 230                 235                 240

Ile Asn Val Val Pro Phe Gly Ile Trp Gln Gln Val Asp Lys Asn Leu
                    245                 250                 255

Arg Phe Met Ile Leu Met Asp Gly Val His Pro Glu Met Asp Thr Cys
                260                 265                 270

Ile Ile Val Glu Tyr Lys Gly His Lys Ile Leu Asn Thr Val Asp Cys
            275                 280                 285

Thr Arg Pro Asn Gly Gly Arg Leu Pro Thr Lys Val Ala Leu Met Met
        290                 295                 300

Ser Asp Phe Ala Gly Ala Ser Gly Phe Pro Met Thr Phe Ser Gly
305                 310                 315                 320

Gly Lys Phe Thr Glu Glu Trp Lys Ala Gln Phe Ile Lys Thr Glu Arg
                325                 330                 335

Lys Lys Leu Leu Asn Tyr Lys Ala Gln Leu Val Lys Asn Leu Gln Pro
            340                 345                 350

Arg Ile Tyr Cys Pro Phe Ala Gly Tyr Phe Val Glu Ser His Pro Ser
        355                 360                 365

Asp Lys Tyr Ile Lys Glu Thr Asn Thr Lys Asn Asp Pro Asn Glu Leu
    370                 375                 380

Asn Asn Leu Ile Lys Lys Asn Ser Asp Val Ile Thr Trp Thr Pro Arg
385                 390                 395                 400

Pro Gly Ala Thr Leu Asp Leu Gly Arg Met Leu Lys Asp Pro Thr Asp
            405                 410                 415

Ser Lys Gly Ile Ile Glu Pro Pro Glu Gly Thr Lys Ile Tyr Lys Asp
                420                 425                 430
```

```
Ser Trp Asp Phe Glu Pro Tyr Leu Glu Ile Leu Asn Ala Ala Val Gly
        435                 440                 445

Asp Glu Ile Phe Leu His Ser Ser Trp Ile Lys Glu Tyr Phe Thr Trp
    450                 455                 460

Ala Gly Phe Lys Asp Tyr Asn Leu Val Val Arg Met Ile Glu Thr Asp
465                 470                 475                 480

Glu Asp Phe Asn Pro Phe Pro Gly Gly Tyr Asp Tyr Leu Val Asp Phe
                485                 490                 495

Leu Asp Leu Ser Phe Pro Lys Glu Arg Pro Gln Arg Glu His Pro Tyr
            500                 505                 510

Glu Glu Ile Arg Ser Arg Val Asp Val Ile Arg His Val Val Lys Asn
            515                 520                 525

Gly Leu Leu Trp Asp Glu Leu Tyr Ile Gly Phe Gln Thr Arg Leu Gln
        530                 535                 540

Arg Asp Pro Asp Ile Tyr His His Leu Phe Trp Asn His Phe Gln Ile
545                 550                 555                 560

Lys Leu Pro Leu Thr Pro Pro Asn Trp Arg Ser Phe Leu Thr Cys Cys
                565                 570                 575

Glu Gln Asn Gly Pro Gly Ile Ser Gln Glu Cys Lys Thr Thr
            580                 585                 590

<210> SEQ ID NO 7
<211> LENGTH: 486
<212> TYPE: PRT
<213> ORGANISM: Homo sapiens

<400> SEQUENCE: 7

Met Asp Glu Asn Asn Gly Leu Leu Leu Glu Leu Asn Pro Pro Asn
1               5                   10                  15

Pro Trp Asp Leu Gln Pro Arg Ser Pro Glu Glu Leu Ala Phe Gly Glu
            20                  25                  30

Val Gln Ile Thr Tyr Leu Thr His Ala Cys Met Asp Leu Lys Leu Gly
        35                  40                  45

Asp Lys Arg Met Val Phe Asp Pro Trp Leu Ile Gly Pro Ala Phe Ala
    50                  55                  60

Arg Gly Trp Trp Leu Leu His Glu Pro Pro Ser Asp Trp Leu Glu Arg
65                  70                  75                  80

Leu Cys Gln Ala Asp Leu Ile Tyr Ile Ser His Leu His Ser Asp His
                85                  90                  95

Leu Ser Tyr Pro Thr Leu Lys Lys Leu Ala Gly Arg Arg Pro Asp Ile
            100                 105                 110

Pro Ile Tyr Val Gly Asn Thr Glu Arg Pro Val Phe Trp Asn Leu Asn
        115                 120                 125

Gln Ser Gly Val Gln Leu Thr Asn Ile Asn Val Val Pro Phe Gly Ile
    130                 135                 140

Trp Gln Gln Val Asp Lys Asn Leu Arg Phe Met Ile Leu Met Asp Gly
145                 150                 155                 160

Val His Pro Glu Met Asp Thr Cys Ile Ile Val Glu Tyr Lys Gly His
                165                 170                 175

Lys Ile Leu Asn Ile Val Asp Cys Thr Arg Pro Asn Gly Gly Arg Leu
            180                 185                 190

Pro Met Lys Val Ala Leu Met Met Ser Asp Phe Ala Gly Gly Ala Ser
        195                 200                 205

Gly Phe Pro Met Thr Phe Ser Gly Gly Lys Phe Thr Glu Glu Trp Lys
    210                 215                 220
```

```
Ala Gln Phe Ile Lys Thr Glu Arg Lys Lys Leu Leu Asn Tyr Lys Ala
225                 230                 235                 240

Arg Leu Val Lys Asn Leu Gln Pro Arg Ile Tyr Cys Pro Phe Ala Gly
            245                 250                 255

Tyr Phe Val Glu Ser His Pro Ser Asp Lys Tyr Ile Lys Glu Thr Asn
            260                 265                 270

Thr Lys Asn Asp Pro Asn Glu Leu Asn Asn Leu Ile Lys Lys Asn Ser
        275                 280                 285

Asp Val Ile Thr Trp Thr Pro Arg Pro Gly Ala Thr Leu Asp Leu Gly
    290                 295                 300

Arg Met Leu Lys Asp Arg Thr Asp Ser Lys Gly Ile Ile Glu Pro Pro
305                 310                 315                 320

Glu Gly Thr Lys Ile Tyr Lys Asp Ser Trp Asp Phe Glu Pro Tyr Leu
                325                 330                 335

Glu Ile Leu Asn Ala Ala Leu Gly Asp Glu Ile Phe Leu His Ser Ser
            340                 345                 350

Trp Ile Lys Glu Tyr Phe Thr Trp Ala Gly Phe Lys Asp Tyr Asn Leu
        355                 360                 365

Val Val Arg Met Ile Glu Thr Asp Glu Asp Phe Asn Pro Phe Pro Gly
    370                 375                 380

Gly Tyr Asp Tyr Leu Val Asp Phe Leu Asp Leu Ser Phe Pro Lys Glu
385                 390                 395                 400

Arg Pro Gln Arg Glu His Pro Tyr Glu Ile His Ser Arg Val Asp
                405                 410                 415

Val Ile Arg His Val Val Lys Asn Gly Leu Leu Trp Asp Glu Leu Tyr
            420                 425                 430

Ile Gly Thr Gln Thr Arg Leu Gln Arg Asp Pro Asp Ile Tyr His His
        435                 440                 445

Leu Phe Trp Asn His Phe Gln Ile Lys Leu Pro Leu Thr Pro Pro Asn
    450                 455                 460

Trp Lys Ser Phe Leu Met Cys Cys Glu Gln Asn Gly Pro Val Ile Leu
465                 470                 475                 480

Gln Glu Cys Lys Thr Thr
                485

<210> SEQ ID NO 8
<211> LENGTH: 24
<212> TYPE: DNA
<213> ORGANISM: Artificial sequence
<220> FEATURE:
<223> OTHER INFORMATION: Synthetic

<400> SEQUENCE: 8
cggctcgagt gagctacatg agat                                          24

<210> SEQ ID NO 9
<211> LENGTH: 24
<212> TYPE: DNA
<213> ORGANISM: Artificial sequence
<220> FEATURE:
<223> OTHER INFORMATION: synthetic

<400> SEQUENCE: 9
cggctcgagt aatcaccaag caaa                                          24

<210> SEQ ID NO 10
<211> LENGTH: 20
<212> TYPE: DNA
```

```
<213> ORGANISM: Artificial sequence
<220> FEATURE:
<223> OTHER INFORMATION: Synthetic

<400> SEQUENCE: 10
ccaggaggag ttaccctgaa                                          20

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
tcaatcaatt gcatgggtct                                          20

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
cgaggacagc ccagagacta                                          20
```

TRANSGENIC MOUSE WITH A HOMOZYGOUS MUTATION IN THE CMAH GENE

RELATED APPLICATIONS

This application is a U.S. National Stage Application filed under 35 U.S.C. 371, which claims priority to International Application No. PCT/US06/22282, filed Jun. 8, 2006, which application claims the benefit of priority to Provisional Application U.S. Ser. No. 60/688,867, which was filed on Jun. 8, 2005, the disclosures of which are incorporated herein by reference.

GOVERNMENT INTERESTS

This invention was made with government support from the National Institutes of Health under grant number R01-CA38701.

TECHNICAL FIELD

This application is in the field of sialic acid chemistry, metabolism, antigenicity, and the production of transgenic non-human mammals with altered sialic acid production. More particularly, this application relates to N-glycolylneuraminic acid (Neu5Gc) being an immunogen in humans, and the production of Neu5Gc-free mammalian products for laboratory and human use.

BACKGROUND OF THE INVENTION

All cells are covered with a dense and complex array of sugar chains. Sialic acids (Sias) are a family of nine-carbon sugars that are typically present at the outermost units of these chains. By virtue of their terminal position, sialic acids act as binding sites for many exogenous and endogenous receptors such as the Influenza viruses and the Siglic family of endogenous proteins. Such sugars are thus useful drug targets for the prevention and treatment of infection. They are also involved in various biological and pathological processes such as neuronal plasticity and cancer metastasis. In many of these instances, the precise structures of the sialic acid and the residues it is attached to play critical roles. Thus, studying sialic acid functions is of great biological importance. In addition, sialic acids can be taken up from certain dietary sources (red meat and dairy products), and may also be associated with certain disease states, such as cancer and heart disease.

Cytidine monophosphate-N-acetylneuraminic acid hydroxylase (CMAH) converts the sialic acid N-acetylneuraminic acid (Neu5Ac) to N-glycolylneuraminic acid (Neu5Gc.) In non-human mammals, Neu5Gc is recognized by a number of endogenous binding proteins, as well as by pathogenic organisms such as bacteria and viruses. Humans are unable to produce endogenous Neu5Gc because of an evolutionary inactivating mutation in their CMAH gene. Specifically, this mutation involves a frame-shifting exon deletion of 92 base pairs in the 5' region that gives rise to a truncated protein that lacks the amino acid residues that are necessary for enzymatic activity (Schlenzka, W., et al., FEBS Lett. (1996) 385: 197-200.) This mutation occurred sometime after the divergence of humans from their last common ancestor, so humans are the only known animals missing a functional CMAH gene (Chou, H-H, et al., Proc. Nat. Acad. Sci. (2002), 99 (18): 11736-11741.) Although the cause for this mutation is unknown, it may have been caused by negative selection of individuals that were CMAH+, because of the recognition of Neu5Gc by pathogens.

Neu5Gc is known to be immunogenic in humans (Noguchi A., et al., J. Biochem. Tokyo (1995), 117 (1): 59-62.) Such immunogenicity is believed to play a role in the immune response observed in humans that come into contact with mammalian products, such as cosmetics, food, mammalian cells and cell products, as well as therapeutic agents derived from non-human mammals or exposed to non-human mammalian products. Attempts have been undertaken to try to diminish the Neu5Gc content of recombinantly produced human glycoproteins in cell lines by altering the cell lines using RNAi to suppress expression of the CMAH gene (Chenu S., et al., Biochim. Biophys. Acta. (2003), 1622 (2): 133-144.)

However, there remains a need to produce biological products for human use that lack Neu5Gc, such as the production of human cells or tissues in the absence of Neu5Gc medium, and by using transgenic non-human mammals lacking a fully functional CMAH gene to produce Neu5Gc products for human use.

SUMMARY OF THE INVENTION

In one aspect of the present invention, there is provided a method for producing animal products devoid of N-glycolylneuraminic acid (Neu5Gc) for human use comprising the steps of: preparing a genetically altered non-human mammal lacking a functional cytidine-5'-monophosphate N-acetyl neuraminic acid hydrolase (CMAH) gene; and extracting at least one animal product from the genetically altered non-human animal (e.g., ovine, bovine, piscine or porcine.)

The CMAH gene may be disrupted by a frame-shift mutation, or via application of a cre-lox system mutation.

In specific examples, the CMAH gene may be mutated in the Rieske iron-sulfur center to diminish gene function, such as at the site of the Cys, His, or both Cys and His residues in the Rieske iron-sulfur center. Alternatively, the CMAH gene may be mutated in at least one of the mononuclear iron center binding sites, in the CMP-Neu5Ac binding site, or in the cytochrome b5 binding site. All these sites are depicted in FIG. 16 and highly conserved in all animal species.

The non-human mammal product produced by the transgenic animal may be selected from the group consisting of: serum, muscle, tissue and milk.

The present invention also relates to a transgenic non-human mammal comprising a CMAH gene lacking a functional copy of at least one of the gene domains associated with enzyme activity selected from the group consisting of: a Rieske Iron Sulfur center, a mononuclear iron center binding site, a CMP-Neu5Ac binding site, and a cytochrome b5 binding site; wherein said mammal produces animal products lacking Neu5Gc.

In one sense, the invention is simply a knockout non-human transgenic mammal that lacks expression of CMAH, which may be CMAH$^{-/-}$.

The present invention also contemplates a non-human transgenic animal that carries germline mutations in a CMAH gene that disrupt CMAH activity, as well as a cell line derived from the knockout animal, which may be selected from the group consisting of: stem cells, epithelial cells and muscle cells.

Also included in the present invention is any animal product obtained from the knockout non-human transgenic animal, which may be, for example, tissue and serum.

In yet another embodiment, the present invention is a human embryonic stem cell line devoid of N-glycolylneuraminic acid (Neu5Gc) comprising: a preselected line of human embryonic stem cells; and a culture medium containing Neu5Gc-non-human mammalian serum from a Neu5Gc null transgenic non-human mammal.

Other aspects of the invention are discussed throughout the specification.

BRIEF DESCRIPTION OF THE DRAWINGS

FIG. 1(A) depicts the DMB-high pressure liquid chromatography (HPLC) profiles of Sia released from membrane fractions. Peaks indicated by an asterisk (*) correspond to Neu5Gc7Ac, Neu5,7Ac$_2$, Neu5,8,9Ac$_3$, Neu5Gc7,9Ac$_2$, and Neu5,7,9Ac$_3$, from left to right. Mass spectrometry (MS) and MS/MS data for the peaks corresponding to DMB-Neu5Gc and DMB-Neu5Ac from the membrane bound Sia of ManNGc and Neu5Gc-fed Caco-2 cells were also obtained (not shown.) FIG. 1(B) depicts the proportion of Neu5Gc (expressed as percent of total Sia) in the different fractions of Caco-2 cells. TH=total homogenate; HMW=high molecular weigh fraction; and LMW=cytosolic low molecular weight fraction.

FIG. 7(A) depicts the Neu5Gc-specific MFI observed in all three different cell types. FIG. 7(B) depicts the percent surface Neu5Gc that was calculated by dividing the non-permeabilized Neu5Gc-specific MFI by the permeabilized Neu5Gc-specific MFI.

FIG. 16 depicts a comparison of the deduced amino-acid sequence of the *A. rubens* CMP-Neu5Ac hydroxylase with several mammalian sequences. The sequences were aligned with CLUSTLAW and subsequently shaded with GENE-DOC. Residues identical in at least five of the six sequences are shaded grey, while homologous residues present in at least five of the six sequences are printed white on dark grey. The hamster sequence is incomplete at the N- and C-termini. Box 1 indicates the binding site of the Rieske iron-sulfur center. Included in Box 1 are the critical Cys, His, Cys and His residues at positions 63 and 65 (at the beginning of Box 1) and positions 84 and 87 at the end of Box 1. These are the liganding residues of the Rieske [2Fe2S]-cluster. Boxes 2 and 5 are the postulated binding sites of a mononuclear iron center. Box 3 is the postulated CMP-Neu5Ac binding site. Box 4 is the postulated site of interaction with cytochrome b5. Underlined amino acids indicate the postulated transmembrane domain of the *A. rubens* hydroxylase. The GenBank accession numbers of the sequences depicted are: mouse, D21826; hamster, AJ242835; pig, Y15010; chimpanzee, AF074481; and macque, AB013814. (Martensen, I., et al., Eur. J. Biochem. (2001) 268 (19):5157-5166.)

FIG. 17 depicts the amino acid sequence of the human CMAH enzyme (UniProtKB/Swiss-Prot accession number Q9Y471. As shown, boxes 2 to 5 that align with the sequences shown in FIG. 16 are identified. Also, as expected, the approximately 92 amino acids that include the Box 1 Rieske iron-sulfur center are missing. (Chou, H.-H., et al., Proc. Natl. Acad. Sci. USA (2002) 99:11736-11741.) Note that the same region is highly conserved in all other species (see above.)

DETAILED DESCRIPTION OF THE INVENTION

Figure 1:
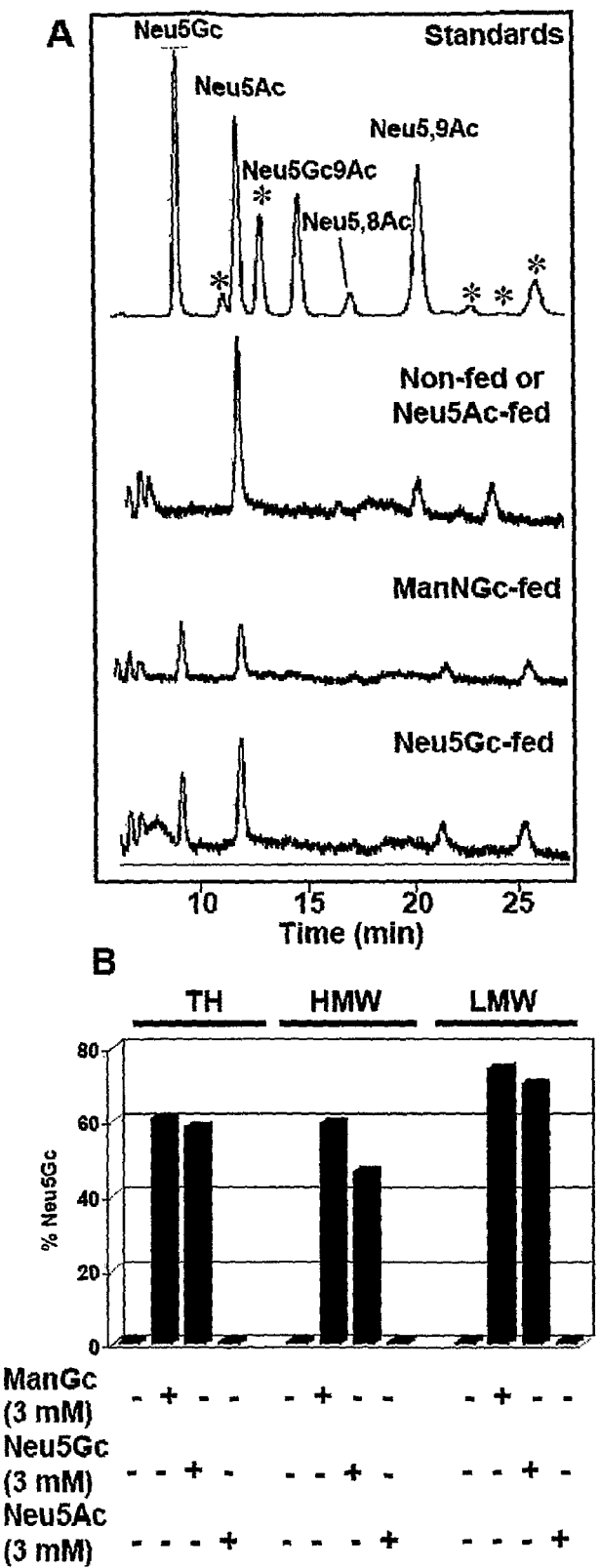
FIG. 1 depicts the incorporation of free Neu5Gc in human epithelial cells. Caco-2 cells were fed or not fed for 3 days with Neu5Gc, ManNGc or Neu5Ac, each at 3 mM final concentration. The cells were harvested and fractionated, and the Sia content of the different fractions of cells was analyzed by 1,2-diamino-4,5-methylenedioxybenzene (DMB) derivatization and liquid chromatography analysis.

This application is in the field of sialic acid chemistry, metabolism, antigenicity, and the production of transgenic non-human mammals with altered sialic acid production. More particularly, this application relates to N-glycolylneuraminic acid (Neu5Gc) being an immunogen in humans, and the production of Neu5Gc-free mammalian products for laboratory and human use.

The three related problems that are addressed by the present invention are: 1) there is a need for Neu5Gc-free animal cell lines, which can be used to produce Neu5Gc biotherapeutic products; 2) there is a need for the production of human cells and tissues for human use, as well as the maintenance of human organs for transplation, under Neu5Gc-free conditions; and 3) there is a need for the production of transgenic Neu5Gc null mammals from which non-human animal products can be derived for human use.

Sialic Acid Chemistry and Metabolism

Sialic acid (Sia) is a generic name for a family of acidic nine carbon sugars typically found as the outermost units of glycan chains on the vertebrate cellular glycocalyx and on secreted glycoproteins. Their location and widespread occurrence on all vertebrate cells allow them to be involved in processes such as ligand-receptor interactions, cell-cell recognition, cell-pathogen binding, inflammatory processes, immune responses and tumor metastases.

There are more than 50 kinds of Sias known in nature. Most are derived via biosynthetic modification of a Sia called N-acetylneuraminic acid (Neu5Ac). The addition of a single oxygen atom to the N-acetyl group of Neu5Ac gives rise to a very common variation called N-glycolylneuraminic acid (Neu5Gc). The surfaces of most primate cell types studied to date are dominated by these two major Sias.

Neu5Gc is perhaps the most widely expressed sialic acid in non-human mammalian cells. While humans are genetically deficient in producing Neu5Gc, small amounts are present in human cells. A dietary origin was suggested by human volunteer studies, and by observing that free Neu5Gc is metabolically incorporated into cultured human cells by unknown mechanisms. Research has shown that the incorporation of Neu5Gc may predominantly originate from dietary sources (Tangvoranuntakul, P. et al. Proc. Natl. Acad. Sci. (USA) (2003) 100:12045-12050.) Red meat from sources such as beef, pork and lamb are particularly rich in Neu5Gc and are likely the primary sources of Neu5Gc in the human diet. Also, dairy products contain Neu5Gc, although at somewhat lower levels than in red meat.

In order for a Sia molecule to get attached to glycoconjugates, it must first be activated by conversion to the sugar nucleotide derivative, cytidine-monophosphate-Sia (CMP-Sia). Thus, Sias are converted to CMP-Sias in the nucleus, which then return to the cytosol in order to be transported into the Golgi apparatus, where they serve as high-energy donors for attaching Sias to newly synthesized glycoconjugates on their way to the cell surface. The biosynthetic transformation of Neu5Ac to Neu5Gc occurs at this sugar nucleotide level, wherein the CMP-Neu5Ac hydroxylase (CMAH) catalyzes the transfer of an oxygen atom to CMP-Neu5Ac, generating CMP-Neu5Gc. CMP-Neu5Gc can then be transported into the Golgi apparatus and used, in the same manner as CMP-Neu5Ac, to add Neu5Gc to newly synthesized glycoconjugates. Indeed, these two nucleotide sugars appear to be used interchangeably by the Golgi CMP-Sia transporter and by the mammalian sialyltransferases, which transfer Sia residues to cell surface and secreted glycoconjugates. Neu5Ac or Neu5Gc molecules that are released from glycoconjugates during lysosomal degradation processes can also be exported back into the cytosolic compartment by a specific transporter. There, they are both available as substrates for conversion to their respective CMP-Sia forms. Again, there appears to be no major difference in their conversion by CMP-Sia synthases. In this manner, Neu5Gc can be "recycled" for repeated use in Golgi sialation reactions.

It has been demonstrated that free Neu5Gc uptake occurs in a variety of mammalian cells and tissues, such as secretory cells, cancer cells, and blood vessels. Inhibitors of certain non-clathrin mediated (i.e. receptor independent) endocytic pathways reduce Neu5Gc accumulation. Studies with human mutant cells show that the lysosomal sialic acid transporter is required for metabolic incorporation of free Neu5Gc. Incorporation of glycosidically-bound Neu5Gc from exogenous glycoconjugates (relevant to human gut epithelial exposure to dietary Neu5Gc) requires the transporter, as well as the lysosomal sialidase, which presumably acts to release free Neu5Gc. Thus, exogenous Neu5Gc reaches lysosomes via pinocytic/endocytic pathways, and is exported in free form into the cytosol, becoming available for activation and transfer to glycoconjugates. In contrast, N-glycolylmannosamine (ManNGc) apparently traverses the plasma membrane by passive diffusion and becomes available for conversion to Neu5Gc in the cytosol. This mechanism can also explain the metabolic incorporation of chemically synthesized unnatural sialic acids.

Sialic Acid Genetics and Immunogenicity

Most normal healthy humans have a certain amount of circulating anti-Neu5Gc antibodies, likely because of the fact that most humans ingest food sources derived from non-human mammals containing high levels of Neu5Gc. Thus, xenogenic (i.e., non-human) culture methodologies may compromise implantation/transplantation success, due to uptake and expression of Neu5Gc on the surface of any tissue developed from human cells exposed to Neu5Gc-containing products. This problem might also affect recombinant soluble biotherapeutic products.

Although Neu5Gc is a major Sia in most mammalian cells, it was long thought to be absent from healthy human tissues (Traving, C., et al. (1998) Cell. Mol. Life. Sci. 54: 1330-1349.) Indeed, humans are genetically unable to synthesize Neu5Gc, due to an exon deletion/frame shift mutation in the human CMAH gene (Varki, A. (2002) Yearb. Phys. Anthropol. 44:54-69; Chou, H. H., et al. (1998) Proc. Ntl. Acad. Sci. USA 95:11751-11756; and Irie, A., et al. (1998) J. Biol. Chem. 273: 15866-15871). It has been estimated that this mutation occurred in the hominid lineage—2.5 to 3 million years ago (Chou, H. H. et al. (2002) Proc. Natl. Acad. Sci. USA 99:11736-11741.) One dramatic consequence of this human-specific genetic defect appears to have been the sudden unmasking of the CD33-related Siglecs during human evolution, since the ancestral condition of these molecules was to recognize Neu5Gc (Sonnengurg, J. L., et al. (2004) Glycobiology 14:339-346.)

Despite the absence of any known alternative pathway for the synthesis of Neu5Gc in humans, various groups have used antibodies to study the expression of Neu5Gc in human tumors, particularly in various carcinomas (Hirabayashy, Y. et al. (1987) Jpn. J. Cancer Res. 78:251-260; Miyoshi, I. et al. (1986) Mol. Immunol. 23:631-638; Marquina, G. et al. (1996) Cancer Res. 56:5165-5171; Carr, A. et al. (2000) Hybridoma 19:241-247; Devine, P. L., et al. (1991) Cancer Res. 51:5826-5836; Kawachi S. et al. (1988) Int. Arch. Allergy Appl. Immunol. 85:381-383; and Higashi, H. et al. (1998) Jpn. J. Cancer Res. 79:952:956.) Recent studies have reexplored these findings, confirming prior reports of Neu5Gc expression in human cancers and extending the finding to normal human tissues, including detecting small amounts of Neu5Gc in epithelial and endothelial cells of normal humans. Definitive confirmation resulted from releasing and purifying sialic acids from such tissues utilizing a fluorescent derivatized form of Neu5Gc by HPLC and mass spectrometry analysis (Tangvoranuntakal, P., et al. (2003) Proc. Natl. Acad. Sci. USA 100:12045-12050.) Moreover, it was shown that exogenously added free Neu5Gc is incorporated into cultured human carcinoma cells in vitro. In addition, oral ingestion studies of Neu5Gc in human volunteers were carried out, providing evidence that the Neu5Gc found in human tissues originates from dietary sources; particularly from red meat and milk products.

Because of the immunogenicity of Neu5Gc in humans, the production of animal products that lack Neu5Gc is, in some ways, half the story. Such animal products if they are to be acceptable for human use must also lack anti-Neu5Gc antibodies which would be carried over to human hosts receiving such animal products. Accordingly, it is desirable to limit the amount of anti-Neu5Gc antibodies in such products. In one instance, it is desirable to limit the amount of anti-Neu5Gc antibodies to within 10% (i.e., a "low" level of antibodies) of the level found in control systems that were prepared in the absence of a source of Neu5Gc. These experiments are described in greater detail elsewhere herein.

Neu5Gc Null Mammals

The mammals that are used in the practice of the invention are those animals generally regarded as useful for the production of mammalian products for human use, such as cosmetics, food stuffs, milk, mammalian cells and cell products, and therapeutic substances. Such mammals include, for example, ovine such as lamb, bovine such as beef cattle and milk cows, piscine and porcine, as well as rodents, such as mice and rats.

In one embodiment, the invention is a method to produce Neu5Gc-free transgenic mammals and products therefrom comprising mutating the CMAH gene such that it produces CMAH with less or no activity, and thereby reducing or eliminating Neu5Gc from the biological material of the non-human mammals. As detailed in FIGS. 16 and 17, the sequences associated with activity (depicted in the boxes) are well characterized and highly conserved. Accordingly, the CMAH gene can easily be mutated, for example, by frameshift mutation or the cre-lox system for deletion mutation, in addition to "knock-in" methods which would eliminate activity, particularly if located in box 1. The biological material derived from such mammals can be virtually any non-human organic material which would otherwise contain Neu5Gc, such as a food stuffs (for example, red meat or a dairy product) or a mammalian derived clinical sample used in human therapy, such as implanted cells or recombinantly produced therapeutic proteins. The clinical sample may be from any non-human mammalian source, such as ovine, bovine, piscine and porcine. Non-human clinical samples can be from any body fluid or tissue, such as serum, muscle tissue and milk, etc. The Neu5Gc-free mammals may be used to produce products for any use by humans, such as cultured human cells produced in laboratories, and cosmetics.

The same methodology used to knock out CMAH in mice is easily adapted for disruption of CMAH gene expression in domesticated animals, because of the high level of homology between CMAH genes in all mammals. For mice, a frameshift mutation, similar to the one found in the human CMAH, was introduced using the cre-lox recombination system. While normal wild-type mice express equal levels of Neu5Gc and Neu5Ac in their muscle tissue, and approximately 5% Neu5Gc in their milk, the transgenic mice exhibit no evidence of Neu5Gc expression in tissues or milk Since the mice are otherwise viable and fertile (as are humans), we can predict that other CMAH null animals will also be the same.

The use of Neu5Gc-free products is useful in several commercial settings. First, since consumption of Neu5Gc may pose a significant risk to human health, meat from Neu5Gc-free animals provides a safer alternative source of red meat. Second, as described in greater detail below, Neu5Gc-free serum can replace normal animal serum, which is currently used to culture human cells in laboratories. Third, the use of Neu5Gc-free bovine products in cosmetics reduces the risk of immune responses against such products.

Culturing Human Cells in Neu5Gc-Free Medium

Considering that most humans also have antibodies to Neu5Gc, incorporation of Neu5Gc is hypothesized to be one of the factors contributing to the health risks associated with high consumption of red meat (such as heart disease and certain types of cancers). In addition, the presence of Neu5Gc in human cells that are cultured in animal products for use in human therapeutic agents is also a potential source of allergenicity. More particularly, when human cells are cultured in serum from animals, they can take up and incorporate Neu5Gc, potentially resulting in immunological rejection if such cells are used for therapy (e.g., transplantation of human embryonic stem cell-derived grafts.) It has now been demonstrated that targeted disruption of the CMAH gene in mice completely abolished the expression of Neu5Gc in all tissues as well as in their secretions. Similar disruption of the CMAH gene in domesticated livestock (cows, pigs, goats, etc.) may provide a source of Neu5Gc-free animal products, which are commonly used as research materials (e.g., serum and cell extracts), as well as in cosmetics.

As described above, by targeting one single gene, CMAH, Neu5Gc can be eliminated from all mammalian tissues and secretions, including serum, muscle tissue and milk. Since Neu5Gc is immunogenic to humans, eliminating CMAH from domesticated animals would provide a source of non-immunogenic Neu5Gc-free products for human cell culture, tissue culture, and even organ preservation. For example, a CMAH null cow will not uptake and incorporate Neu5Gc from ingested meat, milk etc. Accordingly, this invention provides a way of preparing transgenic animals whose serum and other products can be used to produce cell cultures and tissues that will reduce the risk of developing potentially autoreactive antibodies after implantation of such cells and tissues into humans. The absence of Neu5Gc in mammalian serum products used for human cell tissue culture would also provide more human-like growth conditions.

HESCs can potentially generate every body cell type, making them excellent candidates for cell and tissue replacement therapies. HESCs are typically cultured with animal-derived "serum replacements" on murine feeder layers. Both of these are sources of the non-human sialic acid Neu5Gc, against which many humans have circulating antibodies. Both HESC and derived embryoid bodies metabolically incorporate significant amounts of Neu5Gc under standard conditions. Exposure to human sera with anti-Neu5Gc antibodies results in binding of immunoglobulin and deposition of complement, which leads to cell killing in vivo. Levels of Neu5Gc on HESCs and embryoid bodies dropped after culture in heat-inactivated anti-Neu5Gc-antibody-negative human serum, reducing binding of antibodies and complement from high titer sera, while allowing maintenance of the undifferentiated state. Absent the availability of Neu5Gc-free mammalian products, complete elimination of Neu5Gc would likely require using human serum with human feeder layers, ideally starting with fresh HESCs that have never been exposed to animal products.

The pluripotent abilities of HESCs have potential for treating many diseases by transplantation of HESC-derived tissues. While safety is a major issue regarding infection or tumorigenicity, the possibility of rejection is also of concern. Current culture methods using animal products also carry the risk of infection by non-human pathogens. HESC lines are traditionally cultured on mitotically-inactivated mouse embryonic fibroblasts (so-called "feeder layers"), and in a media containing fetal calf serum. To avoid animal serum, certain proprietary serum replacements are sometimes used. However, these also contain animal products. When HESCs are removed from the feeder layer and grown in suspension, they differentiate into aggregates called embryoid bodies (EB). EBs are formed by precursors of several cell lineages and can be induced to differentiate into many cell types. Although the feeder layer is no longer necessary, EBs must still be maintained in "serum replacement" medium, which likewise may contain Neu5Gc positive animal products.

Production of Transgenic Non-Human Animals.

The production of transgenic non-human animals is now a common method used in the laboratory to alter the metabolism of various animals for use as models of particular disease states. For instance, there are insulin free mice, immunologically deficient animals of many species and the like. Accordingly, such methods are commonly practice by those of skill in the art and could easily be adapted to the teachings herein to produce any animal models without undue experimentation. This is especially true since the critical sequences of the HESC gene associated with its active site are well characterized and highly conserved.

In one embodiment, the present invention provides knock-out non-human mammals lacking a functional CMAH. "Knock-out" refers to partial or complete suppression of the expression of a protein encoded by an endogenous DNA sequence in a cell. The "knock-out" can be affected by targeted deletion of the whole or part of a gene encoding a protein in an embryonic stem cell. As a result, the deletion may prevent or reduce the expression of the protein in any cell in the whole animal in which it is normally expressed. For example, a "CMAH knock-out animal" refers to an animal in which the expression CMAH has been reduced or suppressed by the introduction of a recombinant nucleic acid molecule that lacks at least a portion of the genomic DNA sequence encoding CMAH.

"Transgenic animal" refers to an animal to which exogenous DNA has been introduced while the animal is still in its embryonic stage. In most cases, the transgenic approach aims at specific modifications of the genome, e.g., by introducing whole transcriptional units into the genome, or by up- or down-regulating pre-existing cellular genes. The targeted character of certain of these procedures sets transgenic technologies apart from experimental methods in which random mutations are conferred to the germline, such as administration of chemical mutagens or treatment with ionizing solution.

The term "knockout mammal" and the like, refers to a transgenic mammal wherein a given gene has been suppressed by recombination with a targeting vector. It is to be emphasized that the term is intended to include all progeny generations. Thus, the founder animal and all F1, F2, F3, and so on, progeny thereof are included.

The term "chimera," "mosaic," "chimeric mammal" and the like, refers to a transgenic mammal with a knockout in some of its genome-containing cells.

The term "heterozygote," "heterozygotic mammal" and the like, refers to a transgenic mammal with a disruption on one of a chromosome pair in all of its genome containing cells.

The term "homozygote," "homozygotic mammal" and the like, refers to a transgenic mammal with a disruption on both members of a chromosome pair in all of its genome-containing cells.

A "non-human mammal" of the invention includes mammals such as rodents, primates, sheep, dogs (ovine such as lamb, bovine such as beef cattle and milk cows, piscine and porcine.)

Although the invention uses a typical non-human rodent animal (e.g., rats and mice), other mammals can similarly be genetically modified using the methods and compositions of the invention.

A "mutation" is a detectable change in the genetic material in the animal, which is transmitted to the animal's progeny. A mutation is usually a change in one or more deoxyribonucleotides, the modification being obtained by, for example, adding, deleting, inverting, or substituting nucleotides.

Figure 16:
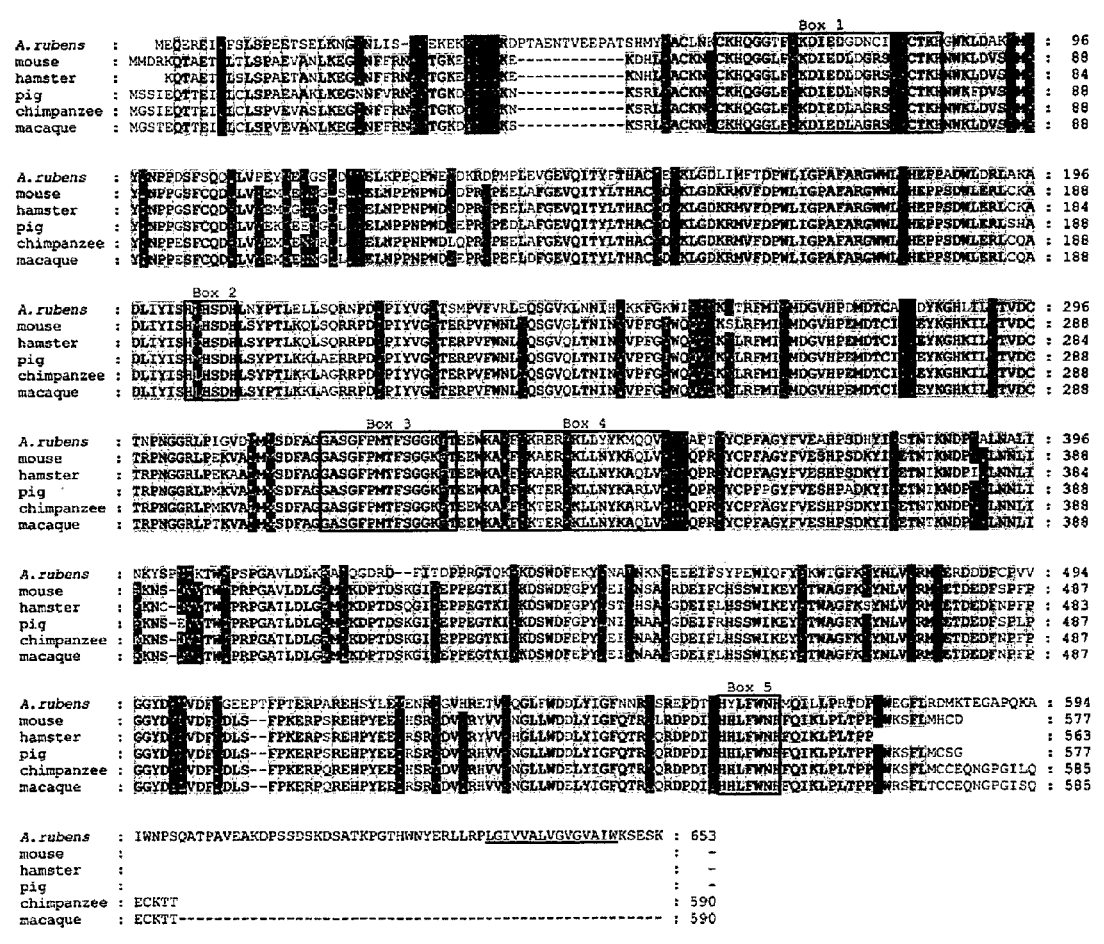

Typically, the genome of the transgenic non-human animal comprises one or more deletions in one or more exons of the genes as depicted in the boxes in FIG. 16.

In principle, knockout animals may have one or both copies of the gene sequence of interest disrupted. In the latter case, in which a homozygous disruption is present, the mutation is termed a "null" mutation. In the case where only one copy of the nucleic acid sequence of interest is disrupted, the knockout animal is termed a "heterozygous knockout animal". The knockout animals of the invention are typically homozygous for the disruption of both CMAH genes being targeted.

It is important to note that it is not necessary to disrupt a gene to generate a transgenic organism lacking functional expression. The invention includes the use of antisense molecules that are transformed into a cell, such that production of an OAT polypeptide is inhibited. Such an antisense molecule is incorporated into a germ cell as described more fully herein operably linked to a promoter such that the antisense construct is expressed in all cells of a transgenic organism.

Techniques for obtaining the transgenic animals of the invention are well known in the art. The techniques for introducing foreign DNA sequences into the mammalian germ line were originally developed in mice. One route of introducing foreign DNA into a germ line entails the direct microinjection of linear DNA molecules into a pronucleus of a fertilized one-cell egg. Microinjected eggs are subsequently transferred into the oviducts of pseudopregnant foster mothers and allowed to develop. About 25% of the progeny mice inherit one or more copies of the micro-injected DNA. Currently, the most frequently used techniques for generating chimeric and transgenic animals are based on genetically altered embryonic stem cells or embryonic germ cells. Techniques suitable for obtaining transgenic animals have been amply described. A suitable technique for obtaining completely ES cell derived transgenic non-human animals is described in WO 98/06834.

Knockout animals of the invention can be obtained by standard gene targeting methods as described above, typically by using ES cells. Thus, the invention relates to a method for producing a knockout non-human mammal comprising (i) providing an embryonic stem (ES) cell from the relevant animal species comprising an intact CMAH gene; (ii) providing a targeting vector capable of disrupting the intact CMAH gene; (iii) introducing the targeting vector into the ES cells under conditions where the intact CMAH undergoes homologous recombination with the targeting vector to produce a mutant CMAH gene; (iv) introducing the ES cells carrying a disrupted CMAH gene into a blastocyst; (v) implanting the blastocyst into the uterus of pseudopregnant female; (vi) delivering animals from said females, identifying a mutant animal that carries the mutant allele and (vii) selecting for knockout animals and breeding them.

A "targeting vector" is a vector comprising sequences that can be inserted into the gene to be disrupted, e.g., by homologous recombination. The targeting vector generally has a 5' flanking region and a 3' flanking region homologous to segments of the gene of interest, surrounding a foreign DNA sequence to be inserted into the gene. For example, the foreign DNA sequence may encode a selectable marker, such as an antibiotics resistance gene. Examples for suitable selectable markers are the neomycin resistance gene (NEO) and the hygromycin P-phosphotransferase gene. The 5' flanking region and the 3' flanking region are homologous to regions within the gene surrounding the portion of the gene to be replaced with the unrelated DNA sequence. DNA comprising the targeting vector and the native gene of interest are contacted under conditions that favor homologous recombination. For example, the targeting vector and native gene sequence of interest can be used to transform embryonic stem (ES) cells, in which they can subsequently undergo homologous recombination.

Thus, a targeting vector refers to a nucleic acid that can be used to decrease or suppress expression of a protein encoded by endogenous DNA sequences in a cell. In a simple example, the knockout construct is comprised of a CMAH polynucleotide with a deletion in a critical portion of the polynucleotide (e.g., the 5' terminus of the CMAH gene) so that a functional CMAH cannot be expressed therefrom. Alternatively, a number of termination codons can be added to the native polynucleotide to cause early termination of the protein or an intron junction can be inactivated. In a typical knockout construct, some portion of the polynucleotide is replaced with a selectable marker (such as the neo gene) so that the polynucleotide can be represented as follows: CMAH 5'/neo/CMAH 3', where CMAH 5' and CMAH 3', refer to genomic or cDNA sequences which are, respectively, upstream and downstream relative to a portion of the CMAH polynucleotide and where neo refers to a neomycin resistance gene.

Proper homologous recombination can be confirmed by Southern blot analysis of restriction endonuclease digested DNA using, as a probe, a non-disrupted region of the gene. Since the native gene, will exhibit a restriction pattern different from that of the disrupted gene, the presence of a disrupted gene can be determined from the size of the restriction fragments that hybridize to the probe.

In an animal obtained by the methods above, the extent of the contribution of the ES cells that contain the disrupted CMAH gene to the somatic tissues of the transgenic animal can be determined visually by choosing animal strains for the source of the ES cells and blastocyst that have different coat colors.

The transgenic animals can contain a transgene, such as reporter gene, under the control of a CMAH promoter or fragment thereof. Methods for obtaining transgenic and knockout non-human animals are known in the art. Knock out mice are generated by homologous integration of a "targeting vector" construct into a mouse embryonic stem cell chromosome which encodes a gene to be knocked out. In one embodiment, gene targeting, which is a method of using homologous recombination to modify an animal's genome, can be used to introduce changes into cultured embryonic stem cells. By targeting a CMAH gene of interest in ES cells, these changes can be introduced into the germlines of animals to generate chimeras. The gene targeting procedure is accomplished by introducing into tissue culture cells a DNA targeting vector that includes a segment homologous to a target CMAH locus, and which also includes an intended sequence modification to the CMAH genomic sequence (e.g., insertion, deletion, point mutation.) The treated cells are then screened for accurate targeting to identify and isolate those which have been properly targeted.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985), J. Embryol. Exp. Mol. Biol. 87:27-45. Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934). Still another ES cell line is the WW6 cell line (Ioffe et al. (1995) Proc. Nat. Acad. Sci. 92:7357-7361.) The cells are cultured and prepared for knockout construct insertion using methods well known to the skilled artisan, such as those set forth in: Teratocarcinomas and Embryonic Stem Cells: A Practical Approach, E. J. Robertson, ed. IRL Press, Washington, D.C. ([1987]; Bradley et al. (1986) Current Topics in Devel. Biol. 20:357-371; and Hogan et al., Manipulating the Mouse Embryo: A Laboratory Manual, Cold Spring Harbor Laboratory Press, Cold Spring Harbor, N.Y. (1986).

A targeting vector construct refers to a uniquely configured fragment of nucleic acid which is introduced into a stem cell line and allowed to recombine with the genome at the chromosomal locus of the gene of interest to be mutated. Thus, a given knock out construct is specific for a given gene to be targeted for disruption. Nonetheless, many common elements exist among these constructs and these elements are well known in the art. A typical targeting vector contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid which encodes a positive selectable marker, such as the neomycin resistance gene (neo). The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for CMAH or other gene of interest to be knocked out. When the resulting construct recombines homologously with the chromosome at this locus, it results in the loss of the omitted coding sequence, otherwise known as the structural gene, from the genomic locus. A stem cell in which such a homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example).

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal which expresses a polypeptide of the targeted gene which is defective in one function, while retaining the unction of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. One skilled in the art will be familiar with useful markers and the means for detecting their presence in a given cell.

As mentioned above, the homologous recombination of the above described "knock out" and "knock in" constructs is sometimes rare and such a construct can insert nonhomologously into a random region of the genome where it has no effect on the gene which has been targeted for deletion, and where it can potentially recombine so as to disrupt another gene which was otherwise not intended to be altered. Such non-homologous recombination events can be selected against by modifying the above-mentioned targeting vectors so that they are flanked by negative selectable markers at either end (particularly through the use of two allelic variants of the thymidine kinase gene, the polypeptide product of which can be selected against in expressing cell lines in an appropriate tissue culture medium well known in the art, i.e. one containing a drug such as 5-bromodeoxyuridine.) Nonhomologous recombination between the resulting targeting vector comprising the negative selectable marker and the genome will usually result in the stable integration of one or both of these negative selectable marker genes and hence cells which have undergone nonhomologous recombination can be selected against by growth in the appropriate selective media (e.g. media containing a drug such as 5-bromodeoxyuridine for example.) Simultaneous selection for the positive selectable marker and against the negative selectable marker will result in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each targeting vector to be inserted into the cell is linearized. Linearization is accomplished by digesting the DNA with a suitable restriction endonuclease selected to cut only within the vector sequence and not the 5' or 3' homologous regions or the selectable marker region.

For insertion, the targeting vector is added to the ES cells under appropriate conditions for the insertion method chosen, as is known to the skilled artisan. For example, if the ES cells are to be electroporated, the ES cells and targeting vector are exposed to an electric pulse using an electroporation machine and following the manufacturer's guidelines for use. After electroporation, the ES cells are typically allowed to recover under suitable incubation conditions. The cells are then screened for the presence of the targeting vector as explained herein. Where more than one construct is to be introduced into the ES cell, each targeting vector can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however the typical method is by microinjection. For microinjection, about 10-30 cells are collected into a micropipet and injected into embryos that are at the proper stage of development to permit integration of the foreign ES cell containing the recombination construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan.

While any embryo of the right stage of development is suitable for use, typical embryos are male. In mice, the typical embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo.) Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2-3 days pseudopregnant.

Offspring that are born to the foster mother may be screened initially for mosaic coat color where the coat color selection strategy (as described above, and in the examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the CMAH gene knocked out in various tissues of the offspring by probing the Western blot with an antibody against the particular CMAH protein, or an antibody against the marker gene product (i.e., the presence of Neu5GC using an antibody as identified in PCT application no. PCT/US2004/022415.) Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of an OAT gene can be controlled by recombinase sequences.

Animals containing more than one knockout construct and/or more than one transgene expression construct are prepared in any of several ways. A typical manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

In another aspect, a transgenic animal can be obtained by introducing into a single stage embryo a targeting vector. The zygote is the best target for micro-injection. In the mouse, the male pronucleus reaches the size of approximately 20 micrometers in diameter which allows reproducible injection of 1-2 pL of DNA solution. The use of zygotes as a target for gene transfer has an advantage in that in most cases the injected DNA will be incorporated into the host gene before the first cleavage (Brinster et al. (1985) Proc. Nat. Acad. Sci. 82:4438-4442.) As a consequence, all cells of the transgenic animal will carry the incorporated nucleic acids of the targeting vector. This will in general also be reflected in the efficient transmission to offspring of the founder since 50% of the germ cells will harbor the transgene.

Normally, fertilized embryos are incubated in suitable media until the pronuclei appear. At about this time, the nucleotide sequence comprising the trans gene is introduced into the female or male pronucleus. In some species such as mice, the male pronucleus is typically used. Typically the exogenous genetic material be added to the male DNA complement of the zygote prior to its being processed by the ovum nucleus or the zygote female pronucleus. It is thought that the ovum nucleus or female pronucleus release molecules which may affect the male DNA complement, perhaps by replacing the protamines of the male DNA with histones, thereby facilitating the combination of the female and male DNA complements to form the diploid zygote.

Thus, the exogenous genetic material is typically added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the a exogenous nucleic acid (e.g., a targeting vector) into the embryo may be accomplished by any means known in the art such as, for example, microinjection, electroporation, or lipofection. Following introduction of the exogenous nucleic acid into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is used. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA will vary depending upon the particular zygote and functions of the exogenous genetic material and will be readily apparent to one skilled in the air, because the genetic material, including the exogenous genetic material, of the resulting zygote must be biologically capable of initiating and maintaining the differentiation and development of the zygote into a functional organism.

The number of copies of a transgene (e.g., the exogenous genetic material or targeting vector constructs) which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of a targeting vector construct, in order to insure that one copy is functional.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of an exogenous polynucleotide (e.g, that of a targeting vector) by any suitable method as described herein. Alternative or additional methods include biochemical. assays such as enzyme and/or immunological assays, histological stains for particular marker or enzyme activities, flow cytometric analysis, and the like.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different knockout, or both. Alternatively, the partner may be a parental line. Where in vitro fertilization is used, the fertilized embryo may be implanted into a surrogate host or incubated in hitro, or both. Using either method, the progeny may be evaluated using methods described above, or other appropriate methods.

Retroviral infection can also be used to introduce a targeting vector into a non-human animal. The developing non-human embryo can be cultured in vitro to the blastocyst stage. During this time, the blastomeres can be targets for retroviral infection (Jaenich, R. (1976) Proc. Nat. Acad. Sci. 73:1260-1264.) Efficient infection of the blastomeres is obtained by enzymatic treatment to remove the zona pellucida (Manipulating the Mouse Embryo, Hogan eds., Cold Spring Harbor Laboratory Press, Cold Spring Harbor, 1986.) The viral vector system used to introduce the targeting vector is typically a replication-defective retrovirus carrying the exogenous nucleic acid (Jahner et al. (1985) Proc. Nat. Acad. Sci. 82:6927-6931; Van der Putten et al. (1985) Proc. Nat. Acad. Sci. 82:6148-6152.) Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the targeting vector (e.g., the exogenous nucleic acids) since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982), supra.)

The cre-lox system, an approach based on the ability of transgenic mice, carrying the bacteriophage Cre gene, to promote recombination between, for example, 34 bp repeats termed loxP sites, allows ablation of a given gene in a tissue specific and a developmentally regulated manner (Orban, et al. (1992) Proc. Nat. Acad. Sci. 89:6861-6865.) LoxP sites can be placed flanking an exon of any given gene. Thus, transgenic mice carrying the Cre gene under the control of a selected promoter can be crossed with transgenic mice carrying a transgene flanked by loxP sites to generate doubly transgenic mice. The pioneering work in developing this system was carried out by Orban et al. (1992) Proc. Nat. Acad. Sci. 89:6861-6865. In one embodiment, the invention uses this technology to target specific tissues in mice (e.g., expressing CMAH), in a developmentally regulated fashion in order to produce a mouse lacking Neu5Gc. This same method can easily be adapted for other mammalian species.

Gene targeting producing gene knock-outs allows one to assess in vivo function of a gene which has been altered and used to replace a normal copy and to generate knockout animals with utility as food. The modifications include insertion of mutant stop codons, the deletion of DNA sequences, or the inclusion of recombination elements (lox p sites) recognized by enzymes such as Cre recombinase. The Cre-lox system as used in one embodiment of the present invention allows for the ablation of a given gene or the ablation of a certain portion of the gene sequence. The Cre-lox system was used to generate CMAH knockout mice exhibiting reduced. Neu5GC.

In another aspect, the invention relates to the use of a CMAH knockout animal, in particular an animal used for food stuff to generate food, food products, pharmaceuticals, and biologics for use.

In a further embodiment, the invention relates to cells and tissues that carry mutations in CMAH. The cells can be primary cells or established cell lines obtained from the transgenic animals of the invention according to routine methods, i.e. by isolating and disintegrating tissue.

Such cells and tissues derived from the animals of the invention, in which the activity of CMAH has been reduced or abolished, are useful in in vitro methods relating to the study of sialic acid moieties, binding and diseases and disorders related thereto.

Cells and cell lines derived from the knockout animals are further useful in screening systems. The invention demonstrates that knockout of CMAH results specific decreases of Neu5Gc. No obvious morphological defects were noted in CMAH knockout mice.

Other Sources for Neu5Gc-Free Cells and Biological Medium.

In addition to producing Neu5Gc-free non-human mammalian products utilizing transgenic techniques, many general cell culture techniques can be used instead. As used herein, the term "devoid of Neu5Gc" intends that the ratio of Neu5Gc to total sialic acids is less than 5%, and even less than 1%. For example, the immunogenicity of Neu5Gc can be exploited by utilizing anti-Neu5Gc antibodies in an affinity column to remove any Neu5Gc present in the products. Alternately, human cells of many varieties, tissues, embryoid bodies, neural lineage cells, carcinoma cells, skin cells, and organs (collectively referred to herein as "cells") can be cultured and preserved in Neu5Gc-environments, so long as they are free of Neu5Gc which can be incorporated therein and are relatively free of anti-Neu5Gc antibodies, which would then be potentially passed on to their human recipients. In another embodiment, serum replacements are now available to culture cells and tissues that lack animal products altogether. Human orthologs and recombinant proteins lacking Neu5Gc are also suitable for incorporation into cell growth medium.

Besides HESCs, other cell types that are within the scope of the present invention include, for example, islet cells, endothelium, liver cells, kidney cells, cardiac cells, fibroblasts, etc. Most notably, however, progenitor cells and pluripotent cells that are not yet completely differentiated are of great use to scientific studies as potential sources for therapeutic treatments involving cellular implantation. In addition, the methods described herein can be used to preserve human organs prior to transplation under conditions that avoid passing on anti-Neu5Gc antibodies or incorporation of additional Neu5Gc.

In most instances, cells are cultured on animal feeder layers, most commonly mouse fibroblasts. However, for reasons discussed elsewhere herein, these feeder layers only serve as additional sources for undesirable Neu5Gc, which can then be incorporated into the cells being cultured. Accordingly, in an attempt to be overcautious, it may be necessary to completely eliminate Neu5Gc by using human serum in the culture medium with human feeder layers, ideally starting with fresh HESCs that have never before been exposed to non-human mammals.

Both the lysosomal sialidase and the lysosomal sialic acid transporter are required for incorporation of glycoprotein-bound NeuGc into human cells. Inhibitors of such enzymes and transporter systems are known. By incorporating these inhibitors, Neu5Gc uptake in cell and tissue cultures, as well as organs being preserved for transplantation can be eliminated.

EXAMPLES

Example I

Mechanism of Uptake and Incorporation of Neu5Gc into Human Cells

Experimental Procedures

Materials—Neu5Gc and Neu5Ac were purchased from Inalco Spa (Milano, Italy) and Pfanstiehl Laboratories, Inc. (Waukegan, Ill.) 1,2-diamino-4,5-methylene dioxybenzene (DMB), chlorpromazine, gemstein, nystatin, amiloride, and saponin were purchased from Sigma-Aldrich (St Louis, Mo.) Premium Human Serum type AB was purchased from Irvine Scientific (Santa Ana, Calif.) Neu5Ac aldolase was purchased from ICN (Costa Mesa, Calif.) All the reagents used were HPLC grade.

Cell Lines—Caco-2 cells (human epithelial cells isolated from a primary colon carcinoma), normal human skin fibroblasts (CCD-919-SK) and chinese hamster ovary (CHO-K1) cells were purchased from ATCC (Manassas, Va.) Mutant human skin fibroblasts (GM05520, GM08496 and GM01718) were obtained from the Coriell Institute for Medical Research (Camden, N.J.) Chimpanzee Fred and human LB EBV-transformed lymphoblasts were a gift from Dr. Peter Parham, Stanford University, CA.

Cell Culture—Caco-2 cells were propagated in alpha-MEM containing GLUTAMAX™ (Invitrogen, San Diego, Calif.) and a mixture of ribonucleosides and deoxyribonucleosides (Gibco/Invitrogen, San Diego, Calif.) supplemented with 20% FCS. All the fibroblast cell lines and CHO-K1 cells were cultured in the same media supplemented respectively with 15% non-heat inactivated FCS or 10% heat inactivated FCS. Chimpanzee Fred and human LB EBV-transformed lymphoblasts were cultured in RPMI-1640 (Gibco/Invitrogen, San Diego, Calif.) supplemented with 10% heat inactivated FCS or 15% human serum. All of the cultures were maintained at 37° C., 5% $CO_2$ atmosphere. In order to deplete any remaining Neu5Gc from FCS, the cells were split and cultured prior to Neu5Gc feeding experiments for at least 4 days in alpha-MEM supplemented with an adequate percentage of heat-inactivated premium human serum instead of FCS. The cells were then maintained under the same conditions during the whole feeding experiment. The human serum was heat inactivated at 56° C. for 30 min. before use.

Preparation of ManNGc from Neu5Gc—ManNGc was prepared by incubating 73 μmoles of Neu5Gc with 624 U Lactate dehydrogenase, 30 μmoles NADH and 10 U Neu5Ac Aldolase, EC 4.1.3.3, in 15 ml of 100 mM potassium phosphate buffer, pH 7.2. The incubation was carried out at 37° C. for 16 h. The ManNGc was separated from any unreacted Neu5Gc by passing the product serially over AG50WX-2 and AGIX-8 (Bio-Rad, Richmond, Calif.) ion-exchange resins. The run-through and 5 column volumes of water washes were collected and concentrated by freeze-drying. The reaction yield (91-98%) was followed by the disappearance of Neu5Gc, using DMB derivatization of the reaction mixture and analysis by HPLC (as described elsewhere herein.)

Preparation and Purification of Sia from Bovine Submaxillary Mucin—A mixture of standard Sias were prepared from bovine submaxillary mucin. Total mucins were extracted from frozen submaxillary glands using known methods. Sias then were released with mild acid, collected by dialysis (1000 daltons molecular-weight-cut-off) and purified on ion exchange columns under conditions determined to minimize loss of O-acetylation.

Neu5Gc and ManNGc Feeding Experiment—Neu5Ac, Neu5Gc or ManNGc were dried, dissolved in the appropriate media supplemented with heat-inactivated human serum, sterilized using a Spin-X® (Corning Inc., Corning, N.Y.) and then added to the cells. The pH of the media containing Sia was adjusted to neutrality using sterilized 1M NaOH before starting the feeding experiment. Cells were cultured in the presence of up to 3 mM free Sia or ManNGc for 1 or 3 days at 37° C. At the end of the feeding, cells were washed with cold PBS, harvested either by scraping or with 2 mM EDTA for fibroblasts, and washed again with cold PBS prior to fractionation.

Fractionation of the Labeled Cells—Washed cell pellets were sonicated into 500 μL of 20 mM sodium phosphate buffer or 20 mM Tris-HCl, pH 7.5, using 4×15 second pulses of a sonicator cell disrupter, model Some Dismembrator (Fisher Scientific, Hampton, N.J.) at a probe setting of 3. The sonicate was centrifuged at 75×g for 15 min., and the pellet Obtained consisted primarily of nuclei and unbroken cells. The pellet contained <5% of the incorporated sialic acid as determined using a radioactive tracer (data not shown.) The supernatant was therefore considered as the "total homogenate" fraction. A portion (20%) of the "total homogenate" fraction was taken for protein quantification and Sia analysis by DMB derivatization and HPLC analysis (as discussed below.) The remainder was centrifuged at 100,000×g for 1 h. The resulting pellet, called the "membrane" fraction, was then resuspended by sonication (15 sec.) in 200 μl of sodium acetate buffer, pH 5.5. The 100,000×g supernatant, called the "soluble" fraction was adjusted to 90% ethanol using absolute ice-cold ethanol, and placed overnight at −20° C. The flocculant precipitate, which represents the "soluble protein" fraction, was washed 3 times with 90%® ice-cold ethanol and then resuspended in 200 μl of water. The supernatant fluid representing the cytosolic low molecular weight (LMW) fraction was dried and brought up in 100 μL with water prior to Sia analysis. All the Sias in these fractions were released with mild acid hydrolysis if necessary and then analyzed by HPLC after DMB derivatization. Protein quantification was performed on the total homogenate, membrane and soluble protein fractions by using the BCA protein assay kit from Pierce (Rockford, Ill.) In some experiments, the resulting data obtained for the Sia bound to the membrane fraction and to the soluble proteins were pooled and presented here as a High Molecular Weight (HMW) fraction.

Sialic Acid Release, DMB Derivatization and HPLC Analysis—The bound Sias from the total homogenate, membrane and soluble protein fractions were released using 2M acetic acid hydrolysis, 3 h. at 80° C. The released Sias, or free Sias, contained in the soluble LMW fraction were passed through a Microcon® YM-10 filter (Millipore, Bedford, Mass.) prior to DMB derivatization, which was done according to Hara et al., 1989. DMB-Sia derivatives from the different fractions were then analyzed by HPLC using a C18 column (Microsorb MV-TM 100 A, Varian, Palo Alto, Calif.) Isocratic elution was achieved using 7% methanol, 8% acetonitrile in water during 50 min. at 0.9 ml/min flow. The eluant was monitored by fluorescence.

Quantification of Sias—For all HPLC chromatograms, the quantification of Sias was done by comparison with known quantities of DMB derivatized Neu5Gc and Neu5Ac used as standards and then reported in terms of pmoles of Sia. For total homogenate, membrane and cytosolic protein fractions, this number was expressed per mg of protein. Due to minor sample-to-sample variations in amounts and recoveries, the data in the Figures is presented as percent of Neu5Gc over total Sias, rather than as absolute amounts.

MS and MS/MS Analysis of DUB Derivatives—In some experiments, the nature of the DMB derivatives of Sias was confirmed by mass spectrometry on a Finnigan MAT HPLC (Thermo, Waltham, Mass.) with online mass spectrometry system using a model LCQ-Mass Spectrometer System A. A Varian C18 column was used and eluted in the isocratic mode with 8% acetonitrile, 7% methanol, 0.1% formic acid in water at 0.9 ml/min over 50 min. The eluant was simultaneously monitored by UV absorbance at 373 nm and by electrospray ionization (ESI) mass spectrometry. The ESI settings used were capillary temperature of 210° C., capillary voltage at 31 V and the lens offset voltage at 0 V. Spectra were acquired by scanning from m/z 150-2000 in the positive ion mode. In some instances, MS/MS was acquired by selecting the parent mass and using a 20% normalized collision energy. Data analysis was performed using the XCALIBUR data analysis program from the instrument manufacturer.

Endocytosis Inhibition Experiments—Caco-2 or normal fibroblast cells were split and cultured in alpha-MEM media supplemented respectively with 20% or 15% human serum for 4 days before starting the endocytosis drug inhibition experiments in order to deplete any Neu5Gc derived from FCS. Cells were then pre-treated for 2 h. with the specific inhibitors under the same culture conditions. Fresh media containing the same amount of inhibitor and 3 mM of Neu5Gc was then added to the cells, which were incubated for 16 h or 3 days and finally harvested and fractionated as described above. Based on known methods, chlorpromazine, genistein, nystatin and amiloride were used at final concentrations of 6~Lg/mL, 200 ItM, 25 pg/mL and 3 niM, respectively.

Western Blot Analysis—Membrane proteins extracted from Neu5Gc-fed, ManNGc-fed or non-fed human wild-type (WT) and mutant fibroblasts were separated by SDS-PAGE electrophoresis using an 8% polyacrylamide gel. The separated proteins were transferred onto a nitrocellulose membrane, which was blocked overnight with tris buffered saline containing 0.1% of Tween-20 (TBS-T.) Immunodetection was then performed using an anti-Neu5Gc antibody (1:10,000 in TBS-T, 3 h., room temperature (RT).) Binding of the anti-Neu5Gc antibody was detected using a secondary horse radish peroxidase (HRP)-conjugated donkey anti-chicken IgY antibody diluted at 1:30,000 in TBS-T for 45 min. at room temperature (RT) (Jackson ImmunoResearch Laboratories, West Grove, Pa.) Final development of the blots was performed using Supersignal West Pico ECL reagent (Pierce, Rockford, Ill.) and X-GMAT Kodak (Rochester, N.Y.) films.

Flow Cytometry—Human WT and mutant fibroblasts grown in media with 10% FCS+20% horse serum for 3 days were lightly trypsinized (0.04% trypsin, 0.53 mM EDTA for 5 min.) to release cells from the flasks. The cells were washed with PBS and then fixed overnight with 1% paraformaldehyde in PBS. Fixed cells were permeabilized or not with 0.1% saponin in PBS at RT for 20 min. Chicken anti-Neu5Gc antibody was added to cells at a 1:200 dilution in PBS and incubated at RT for 30 min. Cells were then washed with PBS and resuspended in FITC-conjugated goat anti-chicken IgY (1 µg/100 µl) (Southern Biotechnology Associates, Birmingham, Ala.) and allowed to incubate for 30 min. at RT. Labeled cells were washed with PBS and resuspended in 500 µl PBS for analysis of FITC fluorescence on a FACS Calibur (BD Biosciences, San Jose, Calif.)

Fluorescence Microscopy—Human WT and mutant fibroblasts were grown on poly-D-lysine-coated glass chamber slides (Nalge Nunc. International, Naperville, Ill.) with media containing 10% FCS+20% horse serum for 4 days. Cells were fixed onto slides using 1% paraformaldehyde in PBS for 30 min. at RT before permeabilizing with 0.1% saponin for 20 min. at RT. Chicken anti-Neu5Gc antibody was then added at 1:50 dilution in PBS along with 1 µg of mouse anti-LAMP-1 (clone H4A3, BD Pharmingen, San Diego, Calif.) and incubated at RT for 1 h. Bound antibodies were then detected with FITC-goat anti-chicken IgY and Cascade Blue (Invitrogen, San Diego, Calif.)-goat anti-mouse IgG (each at 1·µg/100 µl) at RT for 1 h. Cells were washed with PBS and covered with Gel/Mount (Biomedia, Foster City, Calif.) before fluorescence imaging with a Zeiss (Carl Zeiss, Germany) microscope at 400× magnification with emission filters at 400 and 520 nm for Cascade Blue and FITC, respectively.

Results

Free Neu5Gc can be taken up by human epithelial cells from an exogenous source and incorporated into different subcellular fractions. Evidence was presented suggesting that the small amounts of Neu5Gc found in some human tissues originated from dietary sources and showed that human Caco-2 cells (human epithelial cells from a primary colon carcinoma) in culture could metabolically incorporate free Neu5Gc, as determined by a Western blot of a total homogenate using and anti-Neu5Gc antibody. Increasing incorporation of Neu5Gc was found in the total homogenate fraction of the cells over time, with the highest level reached after incubation with 3 mM Neu5Gc for 3 days. Moreover, western blotting with an anti-Neu5Gc antibody demonstrated metabolic incorporation of Neu5Gc into glycoproteins of these cells.

The partitioning of the exogenous Neu5Gc into different subcellular fractions of these cells has also been analyzed. Prior to feeding, Caco-2 cells were split and cultured in human serum instead of FCS in order to eliminate traces of Neu5Gc in the cells. Culture was continued for 3 days in the presence of 3 mM Neu5Gc using 3 mM ManNGc and Neu5Ac as positive controls. Indeed, it was shown that Neu5Ac and ManNGc can be incorporated into cells and that ManNGc or its peracetylated form can be metabolized into Neu5Gc. After the 3 day feeding, the cells were harvested and the Neu5Gc content of the different subcellular fractions were analyzed by DMB derivatization, HPLC, MS and MS/MS analysis. As shown in FIG. 1A, the DMB-HPLC profiles of Sias released from the membranes of Caco-2 cells fed with 3 mM ManNGc or Neu5Gc presented two peaks which correspond to Neu5Gc and Neu5Ac, by comparison with the retention times of standards. Cells that were not fed or fed with Neu5Ac had only one peak corresponding to Neu5Ac. These results were confirmed by LC-MS and MS/MS analysis. DMB-Neu5Gc and DMB-Neu5Ac adducts gave signals at m/z 442/424 and 426/408 respectively, representing molecular ions of DMB-derivatized Neu5Gc and Neu5Ac and their dehydrated forms. LC-MS and MS/MS data obtained on DMB-derivatized Sias released from the membranes of Caco-2 cells non-fed or fed with Neu5Ac gave only a single ion at m/z 426 which can be broken down to 408 by MS/MS, confirming the presence of Neu5Ac and the absence of Neu5Gc. The same analysis on Neu5Gc or ManNGc fed Caco-2 cell membrane Sias gave ions at m/z 442/426, which are respectively dehydrated to 424/408 in MS/MS analysis.

These analyses confirmed the presence of Neu5Gc associated specifically within the glycoconjugates of the membranes of Caco-2 cells fed with ManNGc or Neu5Gc. All other sub-cellular fractions were also studied using the same DMB-HPLC approach. Due to sample-to-sample variations in amounts and recoveries, data is presented in this and subsequent figures as percent of Neu5Gc over total Sias, rather than as absolute amounts. FIG. 1B summarizes the results showing that the total homogenate (TH), high molecular weight fraction (HMW is the combination of membrane and soluble protein fractions) and cytosolic low molecular weight (LMW) fraction contain 58, 46 and 70% Neu5Gc, respectively. In the experiment presented here, the % of Neu5Gc in the membrane fraction of cells fed with Neu5Gc was lower compared to the one obtained for cells fed with ManNGc. This was not always the case, as was observed in other feeding experiments that free Neu5Gc can be as efficient as ManNGc and sometimes even better. The relative percentages obtained for the other fractions (total homogenate, LMW and soluble protein) were similar in several repeated ManNGc and Neu5Gc feeding experiments.

Figure 2:
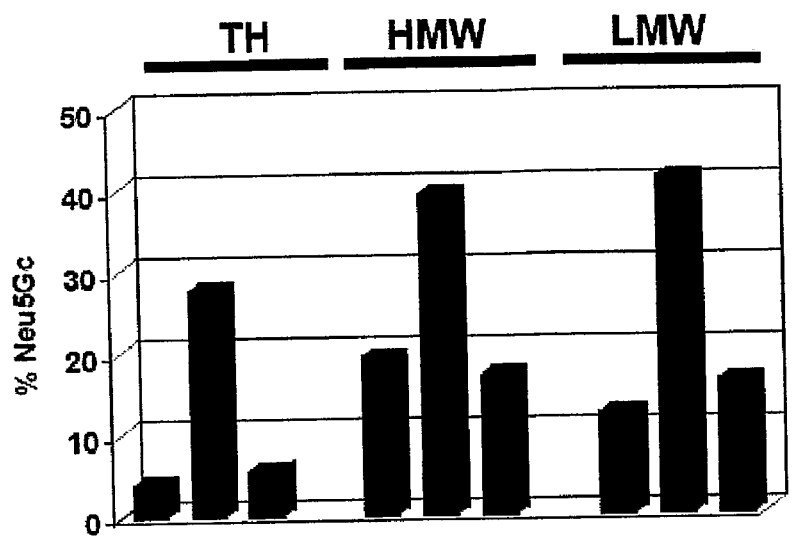
FIG. 2 depicts free Neu5Gc taken up and incorporated into other types of human cells. Human fibroblast and neuroblastoma cells were fed or not fed for 3 days with 3 mM Neu5Gc or Neu5Ac, and the cells were then harvested and fractionated, and the Sia content in the different fractions of cells was analyzed by DMB derivatization followed by HPLC. The proportion of Neu5Gc (expressed as percent of total Sia) of the different fractions from (A) human fibroblasts or (B) human neuroblastomas is shown. TH=total homogenate; HMW=high molecular weight fraction; and LMW=cytosolic low molecular weight fraction.
Figure 2:
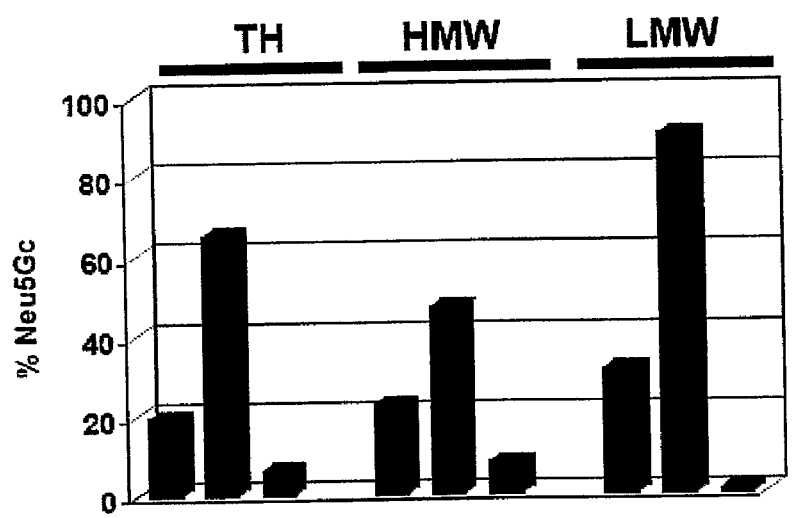

The uptake mechanism of free Neu5Gc is not specific for human epithelial cells. The above experiments showed that free Neu5Gc can be taken up by human epithelial carcinoma cells from the media, and incorporated into different subcellular fractions such as membrane-bound glycoconjugates, soluble proteins, and low molecular weight compounds present in the cytosol. To see if this is a specialized mechanism inhuman carcinoma cells, similar Neu5Gc feeding experiments were done on other human cell types such as normal skin fibroblasts and neuroblastomas. It was found that fibroblast cells can also take up free Neu5Gc from the media, albeit in a less efficient manner. As presented in FIG. 2A, 28%, 39% and 41% Neu5Gc are present in the TH, HMW and cytosolic LMW fractions of the human normal fibroblasts after Neu5Gc feeding. Lower levels (4%, 19%, 12% Neu5Gc) were already present in the same fractions when fibroblast cells were not incubated in presence of 3 mM Neu5Gc. This Neu5Gc is assumed to be derived from Neu5Gc on FCS glycoproteins used for cell culture, prior to feeding experiments Human neuroblastoma cells also incorporate Neu5Gc with an efficiency comparable to the Caco-2 cells (FIG. 2B.) These data indicate that the uptake mechanism of Neu5Gc can also occur in other human cell types, with varying efficiencies.

Figure 3:
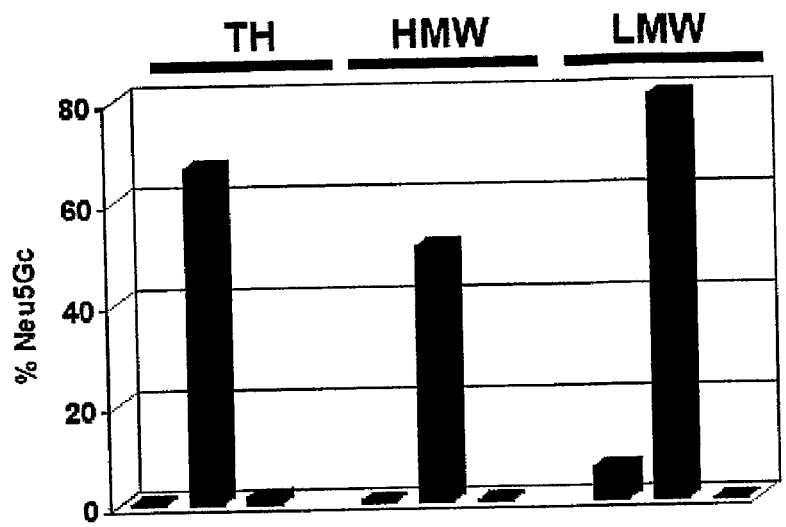
FIG. 3 depicts that the uptake of free Neu5Gc is not specific for human cells. Human and chimpanzee EBV-transformed lymphoblasts were fed or not fed for 3 days with 3 mM Neu5Gc or Neu5Ac, and the cells were then harvested and fractionated, and the Sia content in the different fractions of cells was analyzed by DMB derivatization followed by HPLC. The proportion of Neu5Gc (expressed as percent of total Sia) of the different fractions from (A) human fibroblasts and (B) chimpanzee lymphoblasts is shown. TH=total homogenate; HMW=high molecular weight fraction; and LMW=cytosolic low molecular weight fraction.
Figure 3:
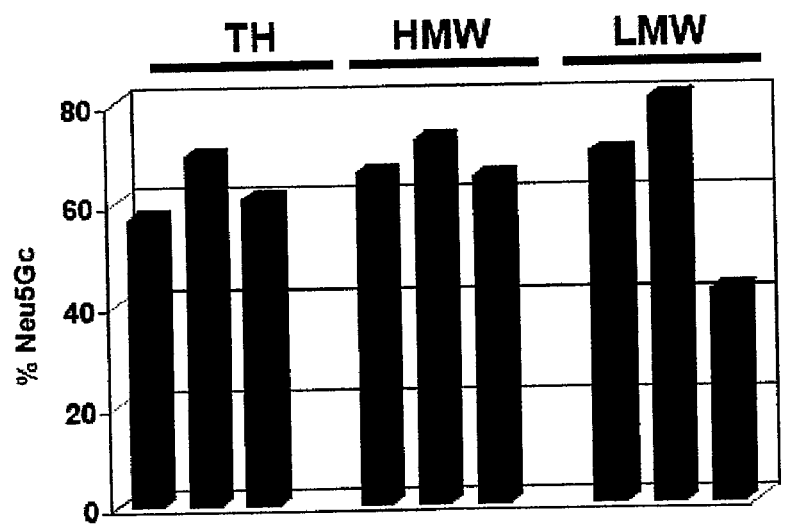

The uptake mechanism of free Neu5Gc is also not specific for human cells. To determine if the uptake mechanism of free Neu5Gc is specific for human cells, Neu5Gc feeding of human and chimpanzee lymphoblasts was compared. Humans are evolutionarily most closely related to the chimpanzee, whose proteins are ~99% identical to those of humans. Of course, great apes such as chimpanzees are able to express Neu5Gc in large amounts because they have an active form of the CMP-Neu5Ac hydroxylase. Prior to the feeding experiment, both cell types were split and cultured in human serum instead of FCS for a couple of weeks. As expected, the Neu5Gc content of chimpanzee lymphoblasts could not be eliminated completely because of the endogenous production of Neu5Gc. After a 3 day feeding of 3 mM Neu5Gc or Neu5Ac, the cells were harvested, fractionated and the Neu5Gc content of the different subcellular fractions were analyzed. As shown in FIG. 3A, the human cells fed with 3 mM Neu5Gc contained 67% Neu5Gc in the TH fraction, 51% in the HMW fraction and 80% in the LMW cytosolic fraction. In contrast, the same cells had almost no detectable Neu5Gc when they were non-fed or fed with Neu5Ac (FIG. 3A.) With chimpanzee cells, we measured baseline levels at 57% Neu5Gc in the TH fraction, 66% in the HMW fraction and 70% in the LMW fraction of non-fed cells (FIG. 3B), representing the endogenous production of Neu5Gc by these cells. When the chimpanzee lymphoblasts were fed with 3 mM Neu5Ac, the percentages of Neu5Gc present in the different fractions changed only minimally (FIG. 3B), presumably because of biosynthetic transformation of Neu5Ac to Neu5Gc occurring at the sugar nucleotide level. When the chimpanzee lymphoblasts were fed with 3 mM Neu5Gc, an increase above the baseline levels was observed to 70% for the TH fraction, 72% for the HMW fraction and 84% for the LMW fraction (FIG. 3B). Similar experiments have been done with Chinese hamster ovary (CHO-K1) cells and with epithelial cells isolated from a spontaneous tumor from a CMAI-I gene knock out mouse. These experiments gave similar results. However, since non-human cells often have large endogenous amounts of Neu5Gc, the consequences are more dramatic in human cells.

Figure 4:
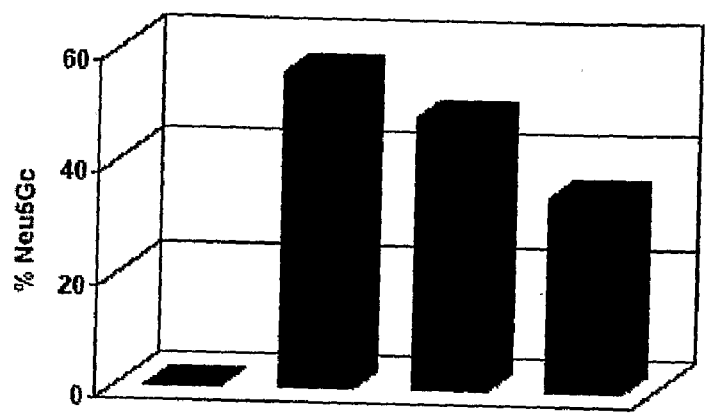
FIG. 4 depicts that free Neu5Ac can compete with free Neu5Gc for incorporation into cells. Caco-2 cells grown in human serum were fed or not fed for 3 days with 3 mM Neu5Gc with or without addition in the media of Neu5Ac at 3 mM or 15 mM final concentration. The cells were then harvested and fractionated. The Sia content in the different fractions of cells was analyzed by DMB derivatization followed by HPLC. The proportion of Neu5Gc (expressed as percent of total Sia) of (A) the total homogenate fraction and (B) the membrane fraction is shown.
Figure 4:
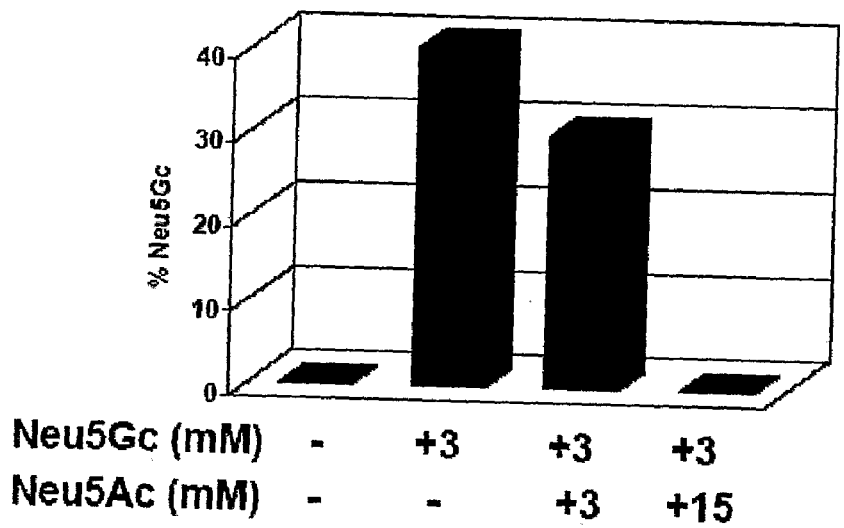

Free Neu5Ac and Neu5Gc are taken up and incorporated by the same pathways. From these data, it appears that Neu5Ac and Neu5Gc can be taken up by many kinds of cells from an exogenous source and incorporated into endogenous glycoconjugates. It has previously been demonstrated that Neu5Gc and Neu5Ac are used interchangeably by essentially all of the steps leading to their final incorporation into glycoconjugates. Higa, H. H. et al. ((1985) J. Biol. Chem. 260: 8838-8849) showed that CMP-Sia synthetases from calf brain and from bovine and equine submaxillary glands both converted Neu5Ac and Neu5Gc to their CMP derivatives efficiently. They also studied six mammalian sialyltransferases purified from porcine, rat, and bovine tissues and concluded that CMP-NeuAc and CMP-NeuGc were equally good donor substrates for all the enzymes. Schauer, R. et al. ((1980) Hoppe-Seyler's Z. Physiol. Chem. 361:641-648) showed that the frog liver CMP-Sia synthetases had very similar Km values for Neu5Ac and Neu5Gc. It has also previously been shown that CMP-Neu5Gc and CMP-Neu5Ac could be taken up by Golgi vesicles and incorporated into endogenous glycoproteins at an approximately equal rate. Similar observations were made by Lepers, A. et al. ((1989) FEBS Lett. 250:245-250) in rat and mouse liver Golgi. Thus, by doing competition experiments in Caco-2 and human normal fibroblast cells, it can be determined whether Neu5Gc and Neu5Ac are taken up and incorporated via the same pathways. Both cell lines gave similar results, and only the results for Caco-2 cells are presented in FIG. 4. Feeding was done for 3 days with 3 mM Neu5Gc in the absence or presence (3 mM or 15 mM) of Neu5Ac in the media. The baseline incorporation of 56% Neu5Gc in the TH was reduced to 48% in the presence of 3 mM Neu5Ac and further decreased to 35% in the presence of added 15 mM Neu5Ac (FIG. 4A). The percentage of Neu5Gc was even more affected in the membrane-bound fraction, reducing from 41% to 29.9% with 3 mM Neu5Ac, and almost to zero in the presence of 15 mM Neu5Ac (FIG. 4B). Since a 5-fold excess of Neu5Ac was enough to abolish the incorporation of Neu5Gc into the membrane fraction of the cells, it is concluded that both molecules likely use the same pathways to enter into human cells and become available for metabolic incorporation. It is of course possible that there are minor differences in utilization of Neu5Gc and Neu5Ac by various enzymes and transporters in the pathways.

Figure 5:
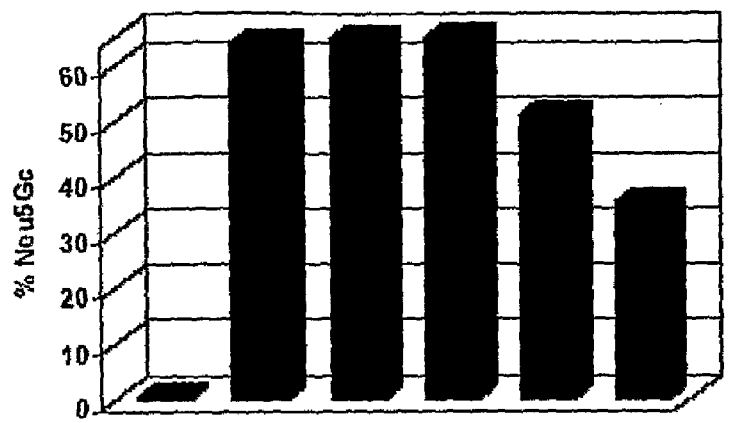
FIG. 5 depicts the uptake of free Neu5Gc by cells occurs via endocytic processes. Caco-2 cells grown in human serum were fed or not fed for 3 days with 3 mM Neu5Gc in the presence or absence of various inhibitors of endocytic pathways. The cells were then harvested and fractionated, and the Sia content in the different fractions of cells was analyzed by DMB derivatization followed by HPLC. The proportion of Neu5Gc (expressed as percent of total Sia) of (A) the total homogenate fraction and (B) the membrane fraction is shown.
Figure 5:
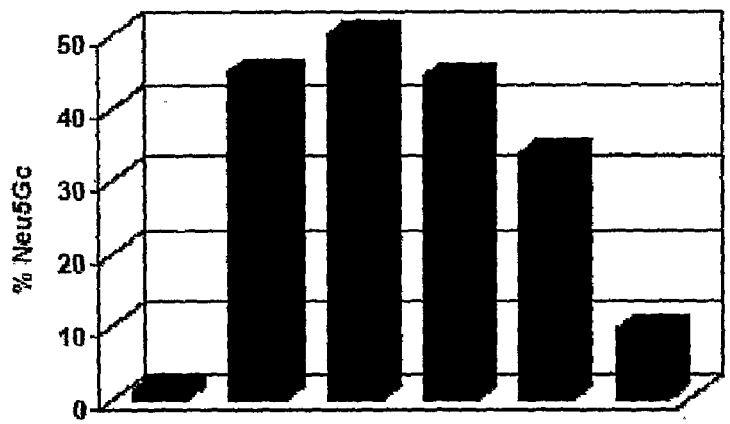

Free Neu5Gc enters into cells via pathways of endocytosis. Negatively charged hydrophilic molecules like sialic acids usually do not cross membranes. To understand how free Neu5Gc enters into cells, the hypothesis that it does so via endocytic pathways was explored. Thus, Neu5Gc feeding experiments on Caco-2 cells were done in the presence of drugs that are known to inhibit various endocytic pathways common to most cell types. Based on known studies in the field, it was decided to use chlorpromazine for blocking the clathrin dependent pathway and nystatin and genistein for the clathrin independent pathways (with an additional specific action of nystatin on caveolar uptake.) Amiloride was used as an inhibitor of fluid phase pinocytosis. All of these drugs were used at concentrations based on prior studies. As before, the Caco-2 cells were incubated in an appropriate media containing human serum instead of FCS and pre-treated with the drug for 2 hours, followed by the addition of 3 mM of Neu5Gc for 16 h. or 3 days. As shown in FIG. 5A, incorporation of Neu5Gc in the TH fraction in the presence of chlorpromazine and nystatin (~65% in both cases) was about the same as for the non-treated Caco-2 cells. In contrast, Neu5Gc incorporation into cells was decreased in the presence of genistein (51%) and much further by amiloride (35.4% Neu5Gc.) Analysis of incorporation into membrane-bound glycoconjugates gave similar results. While there was no obvious difference in the Neu5Gc incorporation for cells cultured without (45%) or with chlorpromazine (50%) or with nystatin (44%), genistein and amiloride caused marked reduction of incorporation to 34% and 10% respectively. These results indicate that exogenous fine Neu5Gc enters cells via clathrin-independent endocytic pathways with a major contribution from fluid phase pinocytosis.

Figure 6:
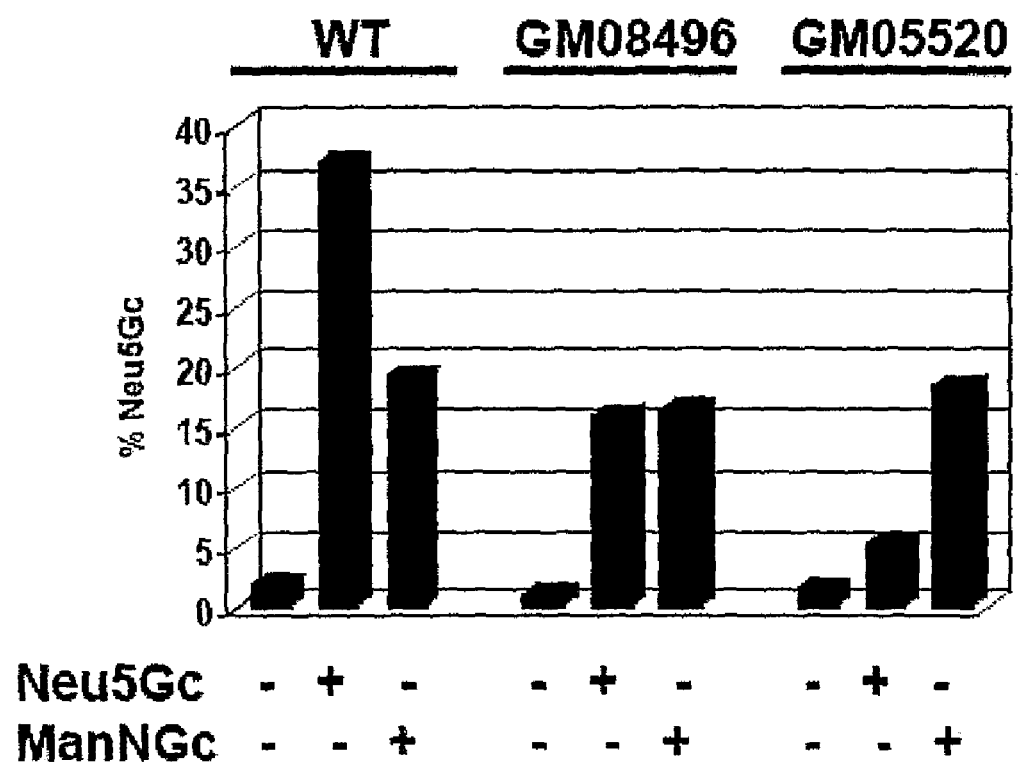
FIG. 6 depicts that the lysosomal sialic acid transporter is involved in the metabolic incorporation of free Neu5Gc. Wild-type (WT) and lysosomal sialic acid transporter mutant human fibroblasts (GM08496 and GM05520) grown in human serum were fed or not fed for 3 days with 3 mM Neu5Gc, ManNGc or Neu5Ac. The cells were then harvested and fractionated, and the Sia content in the different fractions of cells was analyze by DMB derivatization followed by HPLC. The proportion of Neu5Gc (expressed as percent of total Sia) in the membrane fraction is shown.

The lysosomal sialic acid transporter is required for export of free NeuGe from the lysosome to tile Cytosol. Free Neu5Gc molecules entering the cell via endocytic pathways would still be restricted from passively diffusing out of endosomes into the cytosol. It was hypothesized that they would eventually reach the lysosome where they would have the opportunity to utilize the previously known lysosomal sialic acid transporter (58-60) to reach the cytosol. To test this hypothesis, fibroblasts from a patient (GM05520) with a severe infantile form of sialic acid storage disease (ISSD), a disease that is caused by a genetic defect in this transporter, were used. As shown in FIG. 6, the percent of Neu5Gc incorporation into membrane-bound glyconconjugates was reduced from 37% in normal wild-type (WT) fibroblasts to 5% in these mutant cells. As a control, the metabolic conversion of ManNGc into Neu5Gc in these cells was also studied, which presumably occurs following passive diffusion through the plasma membrane, and does not require the lysosomal sialic acid transporter. As predicted, it was found that there was essentially no difference in between normal (19% Neu5Gc) versus mutant fibroblasts (18% Neu5Gc) following feeding with 3 mM ManNGc. Another similar mutant human fibroblast cell line (GM08496) was studied, with a partial inhibition of function of the lysosomal sialic acid transporter. This cell line was isolated from a patient suffering from Salla disease, a milder adult form of sialic acid storage disease. Neu5Gc feeding of these cells resulted in 16% Neu5Gc in membrane-bound glycoconjugates in comparison to the 37% seen in normal WT fibroblasts. Again, feeding with ManNGc gave no obvious change from the control (17% Neu5Gc.) To further confirm that there was a difference in incorporation into glycoproteins, a Western blot analysis was carried out of proteins, extracted from the membranes of wild-type and GM05520 mutant human fibroblasts using an anti-Neu5Gc antibody, with or without prior Neu5Gc or ManNGc feeding. The mutant fibroblasts could not incorporate Neu5Gc into glycoproteins, but could in fact convert it from ManNGc (data not shown.) Taken together, the data confirm the hypothesis that the lysosomal sialic acid transporter plays a crucial role in delivering free sialic acids that enter into cells via endocytosis to the cytosol for activation and incorporation into glycoconjugates.

Both the lysosomal sialidase and the lysosomal sialic acid transporter are required for incorporation of glycoprotein-bound NeuGc into Human cells. Several studies have shown that when human cells are transferred from conventional media containing FCS into serum-free media or human serum, the small amounts of endogenous Neu5Gc in these cells gradually disappear. It has always been assumed that this is because FCS contains many glycoproteins with attached Neu5Gc. However, the pathway by which these glycosidically-bound Neu5Gc molecules enter the cell and eventually become incorporated into endogenous glycoproteins has never been defined. This question is also of direct relevance to human gut epithelial cells, which would be exposed to glycoprotein-bound Neu5Gc of dietary origin (red meat, milk products for example.) Based on the above findings, it is reasonable to hypothesize that the Neu5Gc carrying serum glycoproteins enter the cell via fluid phase pinocytosis, eventually reaching the lysosome where they are exposed to the lysosomal sialidase. The resulting free Neu5Gc in the lysosome would then have the opportunity to use the lysosomal sialic acid transporter to reach the cytosol in order to be salvaged and eventually converted to CMP-Neu5Gc.

To test this hypothesis, the GM05520 mutant human fibroblasts, which are completely deficient in the lysosomal sialic acid transporter, as well as GM01718 mutant human fibroblasts, which have less than 1% lysosomal sialidase activity compared to normal fibroblasts, were used. For these studies, it was important to differentiate between cell surface and internal Neu5Gc. Thus, instead of subcellular fractionation, the method of flow cytometry was utilized, using affinity purified Neu5Gc-specific chicken antibody. As shown in FIG. 7A, after 3 days of feeding with 10% FCS+20% horse serum (both rich sources of glycoprotein-bound Neu5Gc), the total surface expression of Neu5Gc was significantly lower in both mutant fibroblasts compared to WT fibroblasts. Permeabilization of cells revealed similar levels of total Neu5Gc glycoconjugates (FIG. 7A), but the majority in the two mutants was internal (FIG. 7B). To confirm trapping of Neu5Gc glycoconjugates in lysosomes, fluorescence microscopy analysis was performed of permeabilized fibroblasts, co-labelling cells with a known marker for lysosomes, LAMP-1. An even distribution of Neu5Gc staining on WT normal fibroblasts with little co-localization with lysosomes was found. On the other hand, both the lysosomal sialidase and the transporter mutants demonstrated significant accumulation of Neu5Gc glycoconjugates in the lysosomes.

Figure 8:
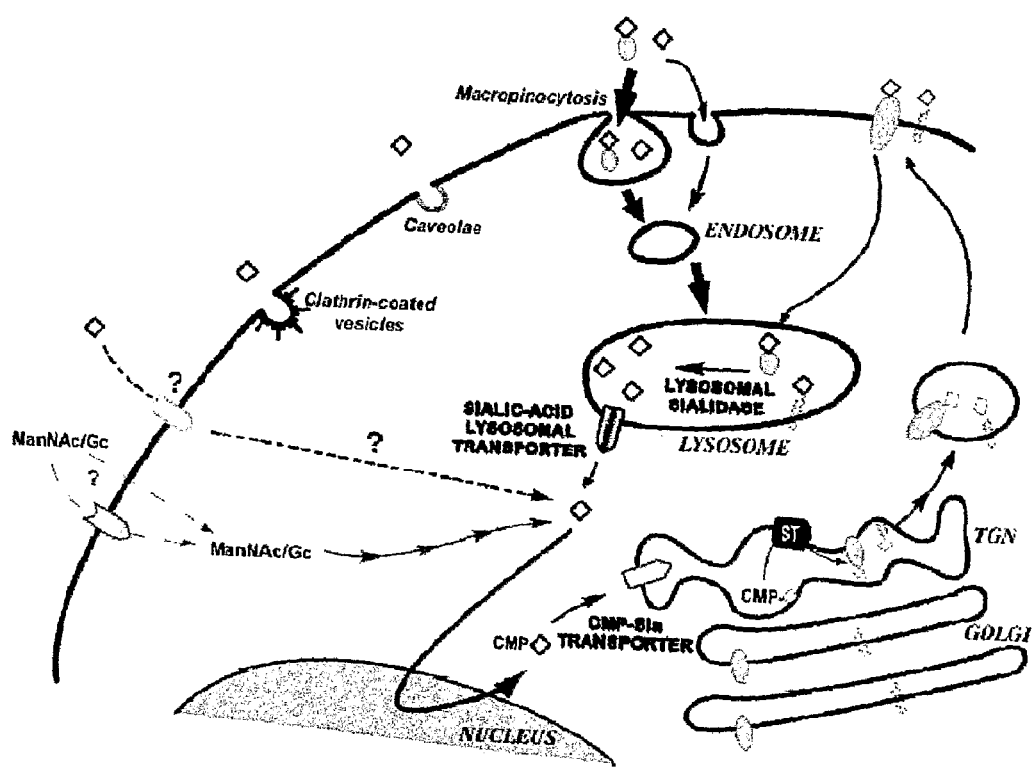
FIG. 8 depicts proposed pathways for the uptake and incorporation of Neu5Gc in human cells as published in Bardor, M., et al., J. Biol. Chem. (2005), 280 (6): 4228-4237.) The proposed model is based on the data presented in this study and upon prior literature. The open diamond represents a Neu5Gc molecule; the shaded oval represents glyproteins; the open bullet represents the sialic acid transporter; and the double zigzags represent ceramide. The thickness of the arrows also suggests the relative importance of various pathways in delivering Neu5Gc into the cell. ST=sialyltransferase and TGN=trans-golgi network.

The results with the sialidase-deficient fibroblasts confirm the hypothesis that this enzyme must act to release free Neu5Gc from glycoproteins and to make it available for metabolic incorporation. The accumulation of Neu5Gc glycoconjugates in the lysosomal transporter mutant was unexpected. A likely explanation is that accumulation of free Sia at a high concentration in the lysosomes inhibits the action of the lysosomal sialidase, resulting in accumulation of glycosidically-bound Neu5Gc. The residual levels of Neu5Gc detected on the surface of both mutant cells might be explained by direct incorporation of gangliosides and GPI-anchored proteins bearing Neu5Gc from the serum. Taken together, these data indicate that bound Neu5Gc molecules that enter into human cells via pinocytosis are released by the lysosomal sialidase and are then transported by the lysosomal sialic acid transporter to the cytosol, where they are available for activation and incorporated into glycoconjugates (FIG. 8.) Of course, depending on the type of glycoprotein involved, bound Neu5Gc could also be delivered to lysosomes via other pathways of endocytosis, e.g., receptor-mediated endocytosis via clathrin-coated vesicles.

It has long been assumed that free sialic acids could not be efficiently incorporated into cells because of their negative charge and hydrophilic nature. Thus, neutral ManNAc has traditionally been used as a precursor to feed cells for conversion into Neu5Ac. The same concept has been applied to various unnatural mannosamine derivatives, and the addition of O-acetyl esters to the hydroxyl groups of mannosamine derivatives has been used to enhance delivery across the plasma membrane. In fact, one early study suggested that radioactive sialic acids could be incorporated into cells, and more recent work of others has shown "efficient" uptake of a variety of kinds of sialic acids into cells. However, the kinetics of incorporation showed no evidence of saturation even at >10 mM concentrations, suggesting that the uptake was not due to a high efficiency cell surface transporter for sialic acids. Studies using a natural sialic acid (Neu5Gc) gave similar results.

Figure 7:
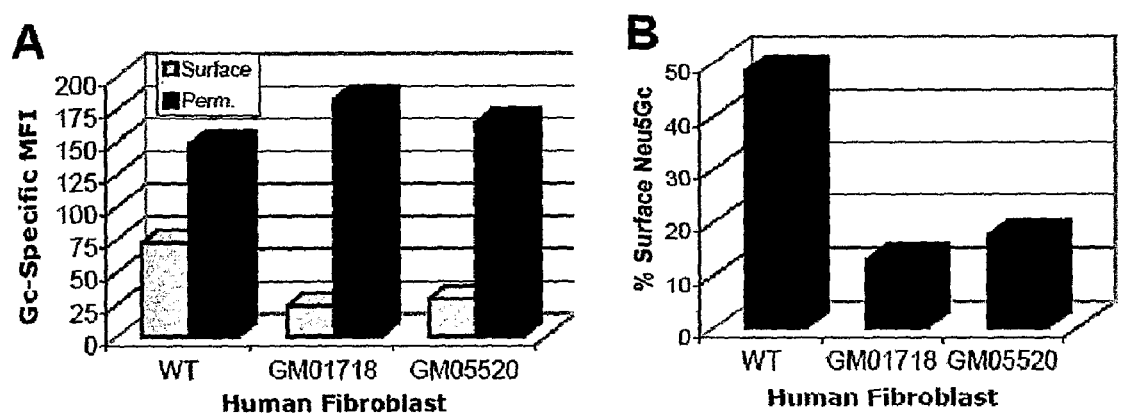
FIG. 7 depicts that both the lysosomal sialidase and the sialic acid transporter are required for metabolic incorporation of glycosidically-bound Neu5Gc from serum glycoconjugates. Wild type (WT) fibroblasts, lysosomal sialidase mutant fibroblasts (GM01718) and Sia transporter mutant fibroblasts (GM05520) were incubated with 10% fetal calf serum (FCS) plus 20% horse serum (which are both rich sources of glycosidically-bound Neu5Gc) for 3 days. Cells were then released from the flasks, fixed and analyzed for binding of a chicken anti-Neu5Gc antibody using a fluorescent labeled anti-chicken antibody, with and without permeabilization by flow cytometry. Neu5Gc-specific MFI is the median fluorescence intensity (MFI) of the labeled anti-chicken antibody staining with the background MFI subtracted out. At least 5000 cells were counted for each staining.

It has been shown that sialic acids from the medium can be taken up into cells via non-clathrin-mediated mechanisms, mostly amiloride-sensitive fluid-phase pinocytosis. The content of the resulting pinocytotic vesicles and endosomes would eventually be delivered to the lysosome, where the previously described sialic acid transporter then delivers the molecules into the cytosol. It has also been shown that the incorporation of glycosidically-bound Neu5Gc from exogenous glycoproteins occurs by similar delivery to the lysosome, and release by the lysosomal sialidase, followed by export into the cytosol (FIGS. 7 and 8.) Once activated to CMP-Neu5Gc, molecules from both sources (free and originally bound) would be indistinguishable from those that were endogenously synthesized by the cells.

Most recently, it has been shown that human embryonic stem cells can incorporate Neu5Gc from medium glycoconjugates, making them targets for the naturally occurring antibodies that circulate in most humans. Preliminary data also suggest that these antibodies could also be related to diseases in intact humans. Thus, the mechanism by which Neu5Gc is incorporated into human cells is of potentially great importance. Further studies of this process are also relevant both to the ongoing attempts by various groups to incorporate different kinds of unnatural sialic acids into cultured cells, and also to efforts to understand how exogenous dietary Neu5Gc gain entry into normal human tissues. In this regard, it is of note that Neu5Gc accumulation appears to be enhanced in naturally occurring tumors, and in fetal tissues. It is suggested that this may be explained by the fact that fluid phase macropinocytosis is enhanced by growth factors, which are expected to be very prominent in these two situations.

Finally, the studies described herein demonstrate, perhaps for the first time, that an extracellular small molecule that cannot cross the plasma membrane is delivered efficiently to the cytosol utilizing fluid pinocytosis and a specific lysosomal transporter. This approach could thus potentially be generalized to any small molecule that has a specific lysosomal transporter, but not a plasma membrane transporter. For example, one could envisage that the neutral sugars GlcNAc and GalNAc, which do not have a high efficiency plasma membrane transporter, could nevertheless be delivered to the cytosol via the lysosomal GlcNAc/GalNAc transporter. The prediction is that adding millimolar concentrations of these sugars into the medium would result in significant delivery to the cytosol.

Example II

Human Embryonic Stem Cells Express an Immunogenic Nonhuman Sialic Acid

The Hl ES cell line (WiCell Research Institute, Inc., Madison, Wis.) cells were cultured on mitotically inactivated (mitomycin C treated) mouse embryonic fibroblasts (MEF, Specialty Media, Phillipsbuurg, N.J.) in DMEMJF12 Glutamax (Gibco), 20% "knockout" serum replacement (Gibco) or pooled human blood-type AB serum (Pel-Freeze, Rogers, Ark.), 0.1 in M non-essential aminoacids (Gibco), 0.1 mM betamercaptoethanol (Gibco), and 4 ng/mL βFGF-2 (R&D Systems, Minneapolis, Minn.). For EB culture, Hl ES cells were grown in suspension for 7-10 days, using the same medium without FGF-2 and 10% serum. Cells were changed to a new dish every day to eliminate eventual fibroblast contamination.

HESC Transfection—Hl HESC were stably transfected to express green fluorescent protein (GFP) by CAG-EGFP SIN lentivirus infection. The SIN lentiviral vector expressing EGFP under control of the CAG promoter was derived from a multiply attenuated HIV vector system, but included a U3 deletion and introduction of a cPPT element. Vectors were produced by triple transduction of HEK 293 cells (Graham et al., J. Gen Virol (1977), 36 (1):59-74) followed by ultracentrifugation and titration. Undifferentiated cells were exposed to the virus at a titer of $0.5 \times 10^{10}$ gtu/mL for 1 hour followed by a 2 day recovery period. EGFP was detected by native fluorescence at day 3 after transduction. Cells expressing EGFP were FACS sorted for uniform EGFP expression. No loss in EGFP expression was observed during propagation or EB differentiation and up to 10 months after transduction. The EGFP positive cells derived from these colonies are thus polyclonal in origin. The GFP positive ES cells maintain a similar phenotype to the wild type cells (SSEA-4, SSEA-3 and Oct4-positive.)

Oct-4 antibody (1:500) was from Santa Cruz (Santa Cruz, Calif.), the other marker antibodies (SSEA-3, TRA-1-60, alkaline phosphatase and nestin) were from Chemicon (Temecula, Calif.; dilution 1:100), and the secondary Cy3 antibody from Sigma (San Louis, Mo.; dilution 1:250). Alkaline Phosphatase (AP) activity was measured using the Vector Red Alkaline Phosphatase substrate kit I from Vector laboratories (Burlingame, Calif.)

Human sera—Sera from several healthy human donors were obtained after written consent and Institutional Review Board approval, and anonymously numbered before further use. Anti-Neu5Gc antibody levels in several serum samples were determined using known methods'. Two specific sera, corresponding to the lowest and highest extremes of the range, were selected for the experiments. Another serum with a high level of anti-Neu5Gc antibodies was also studied with identical results to those presented in the figures.

Determination of Neu5Gc content—Sias from HESC, feeder layer cells, EB or culture medium were released by mild acid, derivatized with 1,2-diamino-4,5-methylene dioxybenzene (DMB) and analyzed by HPLC to determine the percentage of Neu5Gc in total Sias.

Flow cytometry—Cells were harvested into 2 mM EDTA in phosphate buffer (PBS) and washed with PBS. $1 \times 10^5$ cells were incubated with a chicken anti-Neu5Gc (1.5 μg/100 μL) and stained with a donkey anti-chicken IgY conjugated to Cy5 (Jackson, West Grove, Pa.; dilution 1:100 in PBS.) Neu5Gc-specific antibody binding was partially blocked by co-incubation with 1% chimpanzee serum, which (unlike human serum) is rich in Neu5Gc.

For human serum antibody deposition studies, HESC were harvested and exposed to individual human sera. Human IgGs deposited on the cells were stained with an anti-human IgG conjugated to Alexa 594 (Molecular Probes, Carlsbad, Calif.; dilution 1:100 in PBS.) For C3b deposition, HESC were exposed to human serum, then incubated with a goat anti-human C3b (Fitzgerald, Concord, Mass.; dilution 1:100 in PBS) and finally stained with an anti-goat I-G conjugated to Alexa 594 as above.

Cytotoxicity assays—A standard procedure for testing antibody, complement-mediated cytotoxicity after exposure to human sera, was followed. HESCs were harvested and resuspended into $GVB^{2+}$ buffer (Sigma) alone (control) or $GBV^{2+}$ containing 25% human serum. Cells were incubated for 2 h. at 37° C. and gently shaken. Dead cells were stained with propidium iodide (5 μg/mL) and analyzed by FACS. For cytotoxicity assays on the plate, cells were exposed to serum-free HESC culture medium containing 25% of the test human sera. After 30 minutes at 37° C., they were harvested and stained with propidium iodide.

Statistical analysis—Sia content from at least two experiments run in duplicate was analyzed using the T test in Microsoft Excel. Data are expressed as mean±standard deviation.

Figure 9:
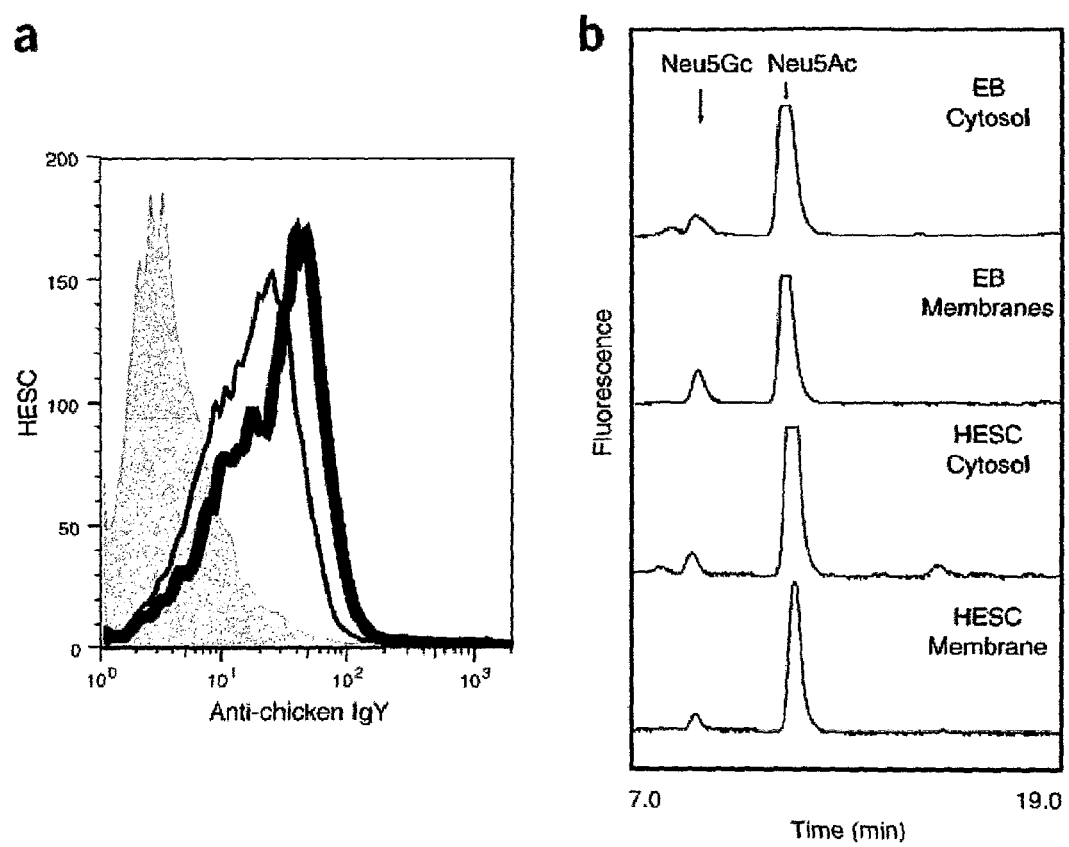
FIG. 9 depicts the detection of Neu5Gc on human embryonic stem cells (HESC) cultured under conventional conditions. Enhanced green fluorescent protein (EGFP) transfected HESCs were grown on a murine feeder layer in a medium containing 20% KNOCKOUT™ (Neu5Gc-rich) serum replacement (Invitrogen Inc., Carlsbad, Calif., and described in WO 98/30679.) a. HESCs were released with 2 mM EDTA and studies were conducted by flow cytometry using a primary affinity-purified polyclonal chicken antibody specific for Neu5Gc, followed by a secondary fluorescent labeled anti-chicken IgY antibody. The gray shaded plot represents the secondary antibody only; the thick line represents both primary and secondary antibody; and the thin line represents cells incubated with the primary antibody in the presence of 1% chimpanzee serum that contains Neu5Gc. b. HESCs were isolated by fluorescent-activated cell sorting (FACS) using the intrinsic EGFP fluorescence. Embryoid bodies (EBs) were derived by removing the feeder layer and growing the HESCs in reduced serum medium for 5 days. Both types of cells (HESCs and EBs) were fractionated into membrane and cytosolic components. Sias were released and analyzed by DMB derivatization and HPLC. A peak corresponding to Neu5Gc is seen in all fractions.

Presence of Neu5Gc on HESC grown under standard conditions—Neu5Gc on HESC was detected using an affinity-purified chicken polyclonal monospecific anti-Neu5Gc antibody. HESC stably expressing EGFP were gated for EGFP-positivity to separate them from contaminating feeder layer fibroblasts. The antibody stained HESCs growing in standard conditions, and binding was partially blocked by Neu5Gc-containing glycoproteins from chimpanzee serum (FIG. 9a.) Blocking was incomplete, likely because not all possible epitopes recognized by the polyclonal antibody are present in chimpanzee serum.

To chemically analyze the Sia content of HESCs, they were separated from the feeder layer fibroblasts by FACS sorting using their EGFP signal. Feeder-layer-free EB derived from HESC were also examined without sorting. Both the membrane and cytosolic fractions from HESC and EB had a peak corresponding to Neu5Gc (FIG. 9b), whose identity was confirmed by electrospray mass spectrometry (data not shown). HESC membranes contained 17.88±1.47 pmoles Sia/μg protein with 9.31±3.70 pmoles Sia/μg protein in the cytosolic fraction. The percentage of total Sias present as Neu5Gc varied from 6-10.5% in the membranes and from 2.5-9% in the cytosolic fraction. EB membranes had 16.59±3.88 pmoles Sia/μg protein with 9.13±0.10 pmoles Sia/μg protein in the cytosolic fraction. The percentage of total Sias present as Neu5Gc in EB varied from 5-17% for the membranes and 6.5-11% for the cytosolic fraction.

Identifying potential sources of Neu5Gc in HESC—Since human cells are unable to synthesize Neu5Gc, the Neu5Gc detected likely originated from elsewhere, eventually being metabolically incorporated by the HESC. As expected for other mammals, Neu5Gc represented 20% of total Sias in the mouse feeder layer (0.92±0.13 nmoles/million cells.) However, uptake from feeder cells cannot explain all the Neu5Gc found in HESC, since removal of the layer to obtain EB did not eliminate it. It was shown that human cells can take up Neu5Gc from the medium and metabolically incorporate it into membrane glycoconjugates. The "serum replacement" containing medium used to support HESC growth was found to contain 35.93 nmoles Neu5Gc/mL, representing 54% of total Sias. The commercial "knockout" serum replacement used for preparing this medium is the major source of Neu5Gc, since it contains 129 nmoles/mL. In contrast, medium without any additives is poor in Neu5Ge (0.008 nmoles/mL.)

Figure 10:
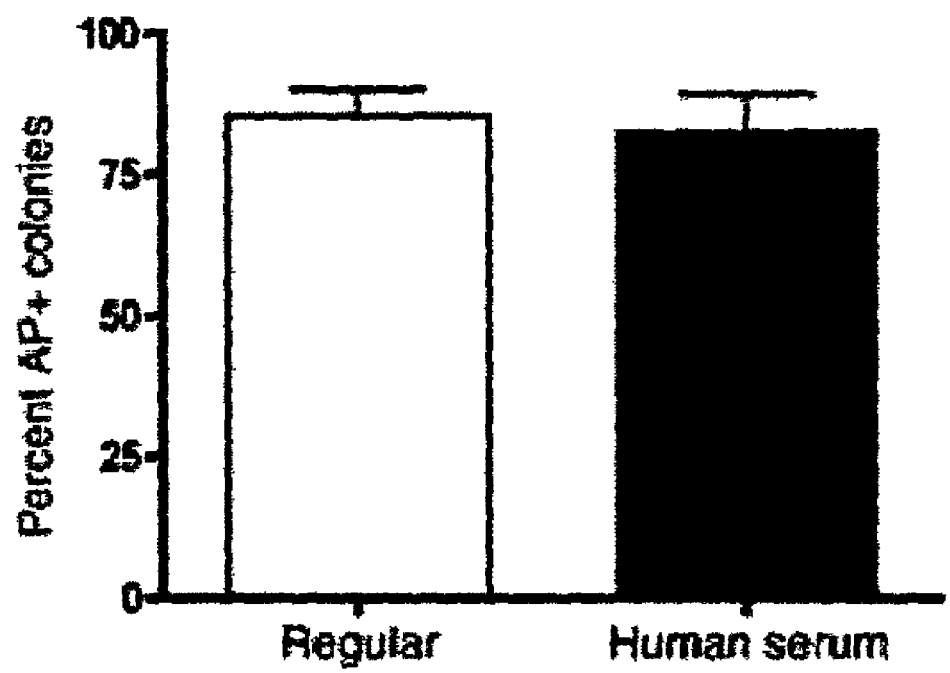
FIG. 10 depicts that HESCs stably expressing EGFP can remain undifferentiated when Neu5Gc-deficient normal human serum (NHS) is substituted for animal-derived culture medium components.

Neu5Gc content of HESC is reduced by growth in heat-inactivated human serum with low anti-Neu5Gc antibodies—Culture in heat-inactivated pooled normal human serum could markedly reduce Neu5Gc in human colon carcinoma cells, apparently due to metabolic replacement by Neu5Ac in the human serum. HESC was therefore incubated in medium containing heat inactivated human serum instead of the standard serum replacement (an approach already suggested by others for different reasons.) First, a lot of pooled human serum was screened and defined in which natural anti-Neu5Gc antibodies were very low (hereafter called NHS.) In case any residual antibodies were active, heat inactivation was used to eliminate complement. HESC incubated in such NHS remained undifferentiated on the feeder layer, expressing typical levels of markers of non-differentiation (alkaline phosphatase, Oct-4, SSEA-3, SSEA-4, TRA-1-60, and TRA-1-81 and lack of all differentiation markers tested (FIG. 10.) After feeder layer removal, these HESC were able to develop into normal EB.

Figure 11:
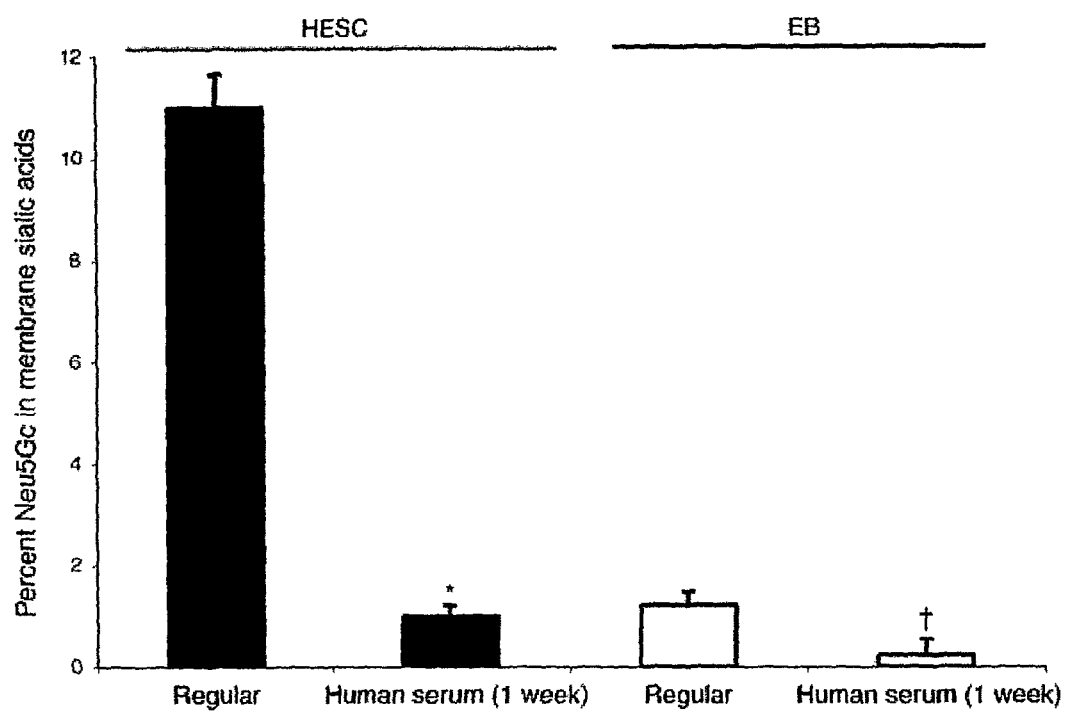
FIG. 11 depicts the effect of growth in normal human serum (NHS) or animal-derived culture medium (Regular) on Neu5Gc content of HESCs and embryoid bodies (EBs).

Neu5Gc incorporation into HESC membranes dropped after 3 days (from ~4 pmoles/μg protein to 0.34±0.06 pmoles/μg protein) and down to 0.13±0.01 pmoles/μg protein after one week (~1% of total Sia as Neu5Gc, see FIG. 11.) The required presence of the mouse feeder layer apparently prevented complete elimination of Neu5Gc from HESC. After growing for 3 days in human serum, some HESC were differentiated into EB either in 10% commercial serum-replacement, or in 10% NHS, without a feeder layer. After one week in serum-replacement, the amount of Neu5Gc on the EB membranes increased (from 0.34±0.06 to 0.40±0.10 pmoles/μg protein.) In contrast, continued incubation in NHS further reduced Neu5Gc levels to 0.047±0.06 pmoles/μg protein.

Figure 12:
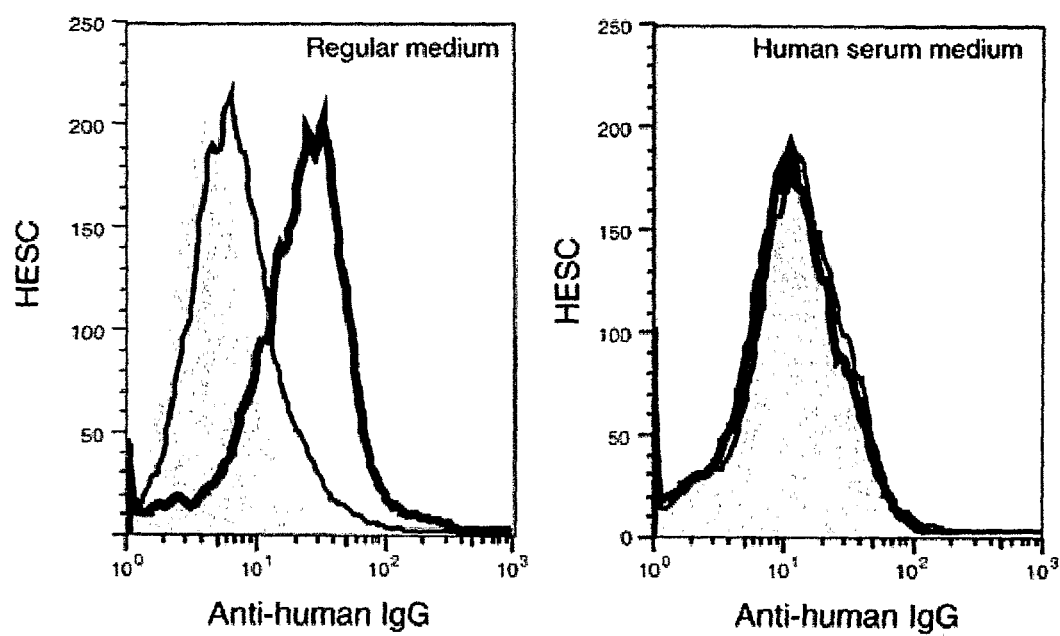
FIG. 12 depicts the binding of "natural" antibodies from sera of normal human donors to HESCs. HESCs were grown in regular medium or in NHS for 5 days. The cells were released with 2 mM EDTA and then exposed to serum from a human with a high level of anti-Neu5Gc antibodies (thick line) or from another individual with a low level of such antibodies (thin line) for 55 min., then stained with a secondary goat anti-human IgG conjugated to Alexa 594 dye (Molecular Probes, Eugene, Oreg.), and studied by flow cytometry, with gating on the EGFP-positive HESCs. The gray shaded plot shows the result with the secondary antibody alone. Immunoglobulin deposition was markedly reduced when cells were first grown in NHS-containing medium for 5 days (although non-specific background levels were increased.) The somewhat higher background seen when HESCs were grown in NHS-containing medium could be due to a non-specific IgG absorption, but it had no major consequences, such as complement deposition.

Natural human anti-Ncu5Gc antibodies bind to HESC and cause complement deposition—Healthy humans have variable levels of "natural" circulating anti-Neu5Gc antibodies. It was determined whether such antibodies could recognize Neu5Gc-containing epitopes on HESC grown under standard conditions. Cells exposed to a high-level anti-Neu5Gc antibody-containing human serum (Hi-GcAbHS) showed human IgG binding (FIG. 12a shows only the EGFP+HESC.) In contrast, staining of cells exposed to a low-level antiNeu5Gc antibody-containing human serum (Lo-GcAbHS) was similar to that of nonexposed controls. Antibody deposition was related to the amount of Neu5Gc on the HESC, since cells growing in NHS did not show any IgG binding when exposed to the same HiGcAbHS (FIG. 12b.)

Figure 13:
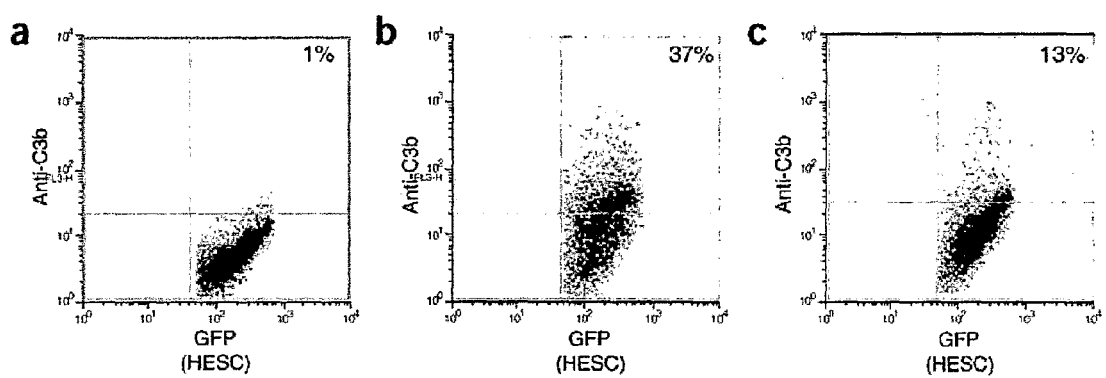
FIG. 13 depicts binding of complement C3b from human sera to EGFP+HESCs. HESCs were grown in regular medium or in NHS-containing medium for 5 days and harvested with 2 mM EDTA. The cells were then exposed to a normal human serum from an individual with a high level of anti-Neu5Gc antibodies for 15 min. at 37° C., and also to the serum from an individual with a low level of anti-Neu5Gc antibodies. Deposited C3b was detected using a goat anti-human C3b, then stained with a goat anti-human C3b conjugated to Alexa 594 and studied by flow cytometry. a. Control cells that where not exposed to any human sera showed very little (1%) positive staining for C3b. b. After exposure to the high level of anti-Neu5Gc antibodies serum, the double fluorescence plot shows that 37% of the EGFP+HESCs grown in regular medium showed positive staining for human C3b. c. In contrast, only 13% of the EGFP+HESCs exposed to the low level of anti-Neu5Gc antibodies serum were positive for C3b.

Cell surface antibody deposition can activate the classical complement pathway, eventually leading to killing or phagocytosis. It was determined whether complement C3b deposition occurred following exposure to Hi-GcAbHS. As before, the data was gated for EGFP+HESC. When HESC were grown under the standard conditions, 37% were positive for C3b (FIG. 13c; compare to 0% background in FIG. 13a.) Only 22% of the cells were positive after exposure to Lo-GcAbHS, with actual levels on individual cells being much lower (FIG. 13b.) (Note that the Y-axis is a log scale.) When HESCs were grown for 5 days in NHS-containing medium, C3b-positivity after exposure to Hi-GcAbHS dropped to 13% (FIG. 13c.) These data are consistent with deposition of anti-human IgG under the same conditions (FIG. 12) and also with the significant reduction in Neu5Gc on the HESC after incubation in human serum-containing medium (FIG. 11.)

Such binding of antibody and complement to HESC would target them for death in vivo, via recognition by macrophages and NK cells. Regardless, attempts were made to directly determine antibody:complement-mediated cytolysis on HESCs in vitro. The standard single cell suspension required for such analyses caused extensive cell death even under control conditions (without serum.) Exposure to Hi-GcAbHS caused increased death above background levels seen with NHS, from 40% to 60-70%. In contrast, the percentage of dead HESCs after exposure to Lo-GcAbHS was similar to that of the control. When the assay was performed directly on the culture dish for shorter time, more HESCs remained alive. Cell death with Hi-GcAbHS was higher than that of the control (14% vs. 10%), whereas the death rate after exposure to Lo-GcAbHS remained unchanged.

HESCs and EB can incorporate the non-human Sia Neu5Gc from the murine feeder layer and/or the medium, leading to an immune response mediated by "natural" anti-Neu5Gc antibodies present in most humans. In effect, HESCs appear like animal cells to the human immune system. Pooled, heat-inactivated human serum selected for low titers of anti-Neu5Gc antibodies could be substituted for the traditional animal serum or serum replacement, supporting the undifferentiated growth of HESCs. This approach markedly reduced the immune response, by reducing the Neu5Gc content on the HESCs.

Most existing HESC lines have been grown or derived with mouse feeder layer. Standard culture conditions also include animal serum, or a serum replacement. It is shown here that the commercial "serum replacement" is also a rich source of Neu5Gc, and both HESCs and EB are able to incorporate it. The composition of this serum replacement is described in PCT WO 98/30679, and includes proteins like transferrin, which are likely to be from animal sources and therefore, would carry Neu5Gc. Human orthologs or recombinant proteins synthesized in bacteria could be used instead.

Many efforts have been recently made to eliminate these animal-derived components. The use of a feeder-free system, such as Matrigel or other components of the extracellular matrices, have been explored. However, feeder-free conditions seem to facilitate in vitro evolution of HESCs, selecting for aneuploid cells. Moreover, many of the medium and matrix components are still from animal sources and contamination with Neu5Gc can be expected.

Human feeders of different origins have also been tried. Richards et al. first reported successful derivation and culture of some HESC lines in the complete absence of non-human components, using feeder layers from human tissues with human serum and supplements, further demonstrating the ability to develop teratomas, i.e., confirming the maintenance of pluripotentiality. It was also noted that human serum did not cause any change in the undifferentiated state of the HESCs. Others have also tried similar xeno-free techniques on hematopoietic stem cells by growing them on human stromal cells and using medium containing human AB serum. Of course, the use of an "all-human" environment carries a different set of risks (unexpected contamination with novel or newly emerging pathogens).

There are also potential implications for the incorporation of Neu5Gc with regard to general HESC biology. Many characteristic markers of HESC(SSEA-3, SSEA-4, TRA-1-60, and TRA-1-81) are glycolipids or glycoproteins, many of which can carry Sias. SSEA-4, which is highly expressed even in long-term cultures of HESCs, is the sialylated form of the globo-series glycolipid SSEA-3 (Gb5.) TRA-1-60 is a sialylated keratan sulfate protein and the TRA-1-81 epitope became accessible only after sialidase treatment. Neural lineage cells derived from EB express the polysialylated form of NCAM, as well as the antigen A2B5, which corresponds to polysialylated gangliosides. Since Sias are involved in self-recognition events, the presence of Neu5Gc instead of Neu5Ac could lead to unexpected impairments of cell function and tissue development.

Another possible solution is growth in heat-inactivated serum from the actual patient who is going to receive the therapy. Similar alternatives have been suggested for hematopoietic stem cells. Even if the patient serum contains anti-Neu5Gc antibodies, heat inactivation could prevent complement activation, until such time as the pre-existing Neu5Gc in the HESCs is metabolically eliminated by the Neu5Ac in the serum. An added advantage to this approach is that it would screen for allogeneic cytotoxic antibodies in the recipient's serum.

Example III

Elimination of N-Glycolylneuraminic Acid Hydroxylase in a Mouse Model

Material and Methods

Generation of targeting construct pFlox-Ex-SL for elimination of CMAH expression. A 10 kb genomic DNA region spanning the CMAH gene that includes the 92 bp corresponding to exon 6 of the murine CMAH was isolated from a BAC clone by digesting the clone with EcoRI with subsequent Southern Blotting using a radiolabeled probe corresponding to exon 6. The 10 kb piece was subcloned into pBluescript II KS+, generating the construct pBS-35. Mapping of the restriction sites of the 10 kb piece was performed by digesting pBS-35 with various restriction enzymes. A 535 bp piece containing exon 6 was isolated from pBS-35 by digesting with NheI and XbaI, and cloned into the BamHI site in the pFlox vector. A 1150 bp intronic region directly upstream of the 535 bp piece was isolated by digesting with NheI and subcloning into the pBluescript II KS+ vector. This was then used for PCR using forward primer CGGCTCGAGTGAGC-TACATGAGAT and reverse primer GGGCTCGAGTAAT-CACCAAGCAAA, thereby adding XhoI restriction site the ends of the 1150 bp piece. The PCR product was subcloned into pBluescript II KS+ vector, which was then digested with XhoI and cloned into the Xho site in the pFlox-Exon vector, creating the pFlox-Ex-S vector. Next, a 4850 bp piece directly downstream of the 535 bp piece was excise from pBS-35 by digesting with XbaI and NheI and cloned into the XbaI site in pFlox-Ex-S vector, generating the final targeting construct, pFlox-Ex-SL.

Generation of CMAH null mice. pFlox-Ex-SL plasmid DNA was purified by a standard cesium chloride method and linearized by digestion with restriction enzyme Not I. The solution containing digested plasmid DNA is then subjected to sequential phenol, 1:1 phenol:chloroform, and chloroform extraction. The aqueous phase containing the linearized DNA is then subjected to sodium acetate precipitation. The resulting DNA pellet is washed 2 times in ice-cold 70% ethanol, air dried, and resuspended in TE. The generation of the transgenic mice was performed by the UCSD Transgenic Mouse Core. In brief, the linearized transgenic constructs were electroporated into embryonic stem cells (ES cells) isolated from the 129/SvJ mouse strain. The ES cells then underwent drug selection, subclone isolation, and growth of isolated clones. Each clone was grown in triplicate plates, one that was kept by the Core as a master plate that was frozen at −80° C. and two that were returned to investigators for the identification of homologous recombinants. DNA was purified from each clone and subjected to screening by PCR and Southern Blot analysis as described below. Homologous recombinants were thawed, expanded, and reconfirmed by PCR and Southern Blot analysis. For the generation of the CMAH null mouse, homologous recombinant clones were subjected to transfection with Cre-recombinase expression vector, underwent gancyclovir drug selection against the presence of thymidine kinase (TK), subclone isolation, and growth of isolated clones. The desired type of recombination was then identified by PCR analysis. Karyotyping was then performed and two of the best clones were selected for blastocyst injection. Chimeric mice were then generated and bred to C57Bl/6 females to allow germline transmission of the transgene.

PCR genotyping analysis of CMAH null mice. To genotype the mice, DNA isolated from toe clips were used for PCR analysis. Toe clips performed to mark the identity of the mice were collected and digested in 20 ul of buffer containing 50 mM Tris, pH 8.0, 20 mM NaCl, 1 mM EDTA, 1% SDS, and 250 ug/ml Proteinase K at 55° C. until the soft tissue dissolved. The sample was then diluted with 180 ul of water and boiled to inactivate the enzyme. For genotyping of CMAH null mice, PCR primers UpExon6 (CCAGGAGGAGTTAC-CCTGAA), Exon6#2 (TCAATCAATTGCATGGGTCT), and DwExon6 (CGAGGACAGCCCAGAGACTA) were designed based on the published murine CMAH sequence. Analysis was performed using the following PCR cycle: 94° C. for 5 min; 40 cycles of 94° C. for 30 sec, 53° C. for 30 sec, and 72° C. for 1 min; and 72° C. for 5 min. A PCR product of 305 bp is generated from the deletion allele while a product of 490 bp is generated from the wild-type allele.

Southern blot analysis of the CMAH null mice. To genotype the mice, DNA isolated from tail clips were analyzed by PCR. Tail clips were digested overnight at 55° C. in buffer containing 10 mM Tris-HCl, pH 8.0+1 mM EDTA (TE), 1% SDS, 140 mM NaCl, and 0.3 mg/ml Proteinase K. A solution of TE, 5.3M NaCl, and chloroform was the added. The genomic DNA in the upper aqueous phase was subjected to ethanol precipitation and resuspended in TE.

DMB-HPLC analysis of Neu5Gc content in cells and tissues. Cells or tissues were homogenized and subjected to acid hydrolysis using 2M acetic acid at 80° C. for 3 h to release sialic acids from cellular glycoconjugates. After centrifugation at 20,000 g, the supernatant was filtered through a Microcon 10 unit, dried down, and reconstituted in water. Aliquots were derivatized with 1,2-diamino-4,5-methylene dioxybenzene (DMB) and analyzed by HPLC (DMB-HPLC). To remove O-acetyl esters, samples were incubated with 0.1 M NaOH for 30 min at room temperature to remove base-labile O-acetyl esters.

Immunohistochemistry using the anti-Neu5Gc antibody. Tissues were collected from autopsies or unused pathological material frozen in OCT compound and archived at −70° C. Frozen tissue sections were air-dried for 30 min, fixed in 10% buffered formalin for 30 min, endogenous peroxidase activity quenched and non-specific binding sites blocked with 5% (Neu5Gc free) human serum in PBS for 30 min. Sections were then incubated with the anti-Neu5Gc antibody in 5% human serum/PBS at a 1:200 dilution at RT for 2 h. After washing, HRP-conjugated donkey anti-chicken IgY antibody in 5% human serum/PBS at a 1:100 dilution was applied for 1 hr. Control sections were incubated with secondary reagent only or a control chicken IgY antibody. Specific binding was detected using the Nova Red substrate kit.

Results

Figure 14:
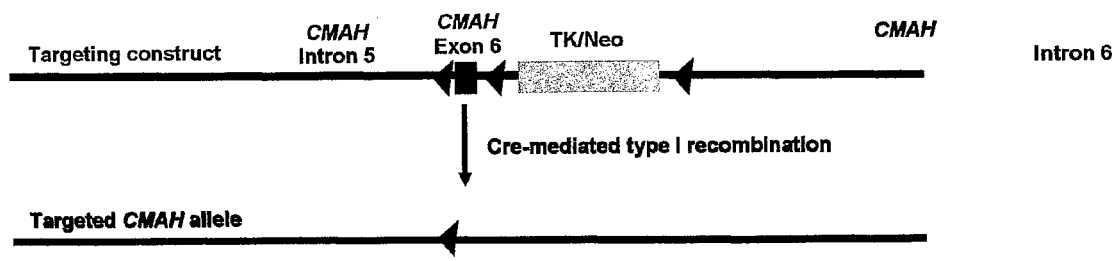
FIG. 14 depicts the targeting construct for inactivation of the CMAH enzyme in the mouse and final targeted Cmah allele. A 10 kb genomic DNA region spanning the Cmah gene that includes the 92 base pairs corresponding to exon 6 of the murine Cmah was used to generate the targeting construct pFlox-Ex-SL for elimination of CMAH enzyme activity by disabling this 92 base pair region that encodes the active site of the CMAH enzyme.

Generation of CMAH null mice—To investigate physiological functions of Neu5Gc in vivo, mice were generated that were deficient in CMP-N-acetylneuraminic acid hydroxylase (CMAH) activity. The original goal was to produce CMAH conditional mutant mice using the Cre/loxP system. Thus, a targeting vector, pFlox-Ex-SL, was first prepared in which exon 6 of CMAH and the TK/Neo cassette, are flanked by loxP sites (FIG. 14). The targeting vector was electroporated into ES cells and 1, out of 245 clones was identified as a homologous recombinant by Southern blot and PCR analysis. This clone was transfected with a Cre-recombinase expression vector and 0 out of 150 clones had undergone type II recombination that would only delete the TK/Neo cassette. Due to subsequent difficulties obtaining type II recombinants, we chose to select only two type I recombinants (where both the exon 6 and the TK/Neo cassette were deleted) for blastocyst injection into C57BL/6 females. Chimeric mice were bred and one clone achieved germline transmission.

Mice deficient in CMAH were viable and fertile and showed no gross morphological or histological abnormalities in many organs studied, and their growth was equivalent to that of wild-type littermates (data not shown). Transmission of the null allele occurred at the expected Mendelian frequency in pups resulting from heterozygous breeding as depicted below in Table 1:

TABLE 1

Genotypes of litters from intercrosses of CMAH heterozygous mice

| | No. (%) of pups with genotype |
|---|---|
| Wild type (+/+) | 12 (20) |
| Heterozygous (+/−) | 38 (63) |
| Homozygous (−/−) | 10 (17) |

Figure 15:
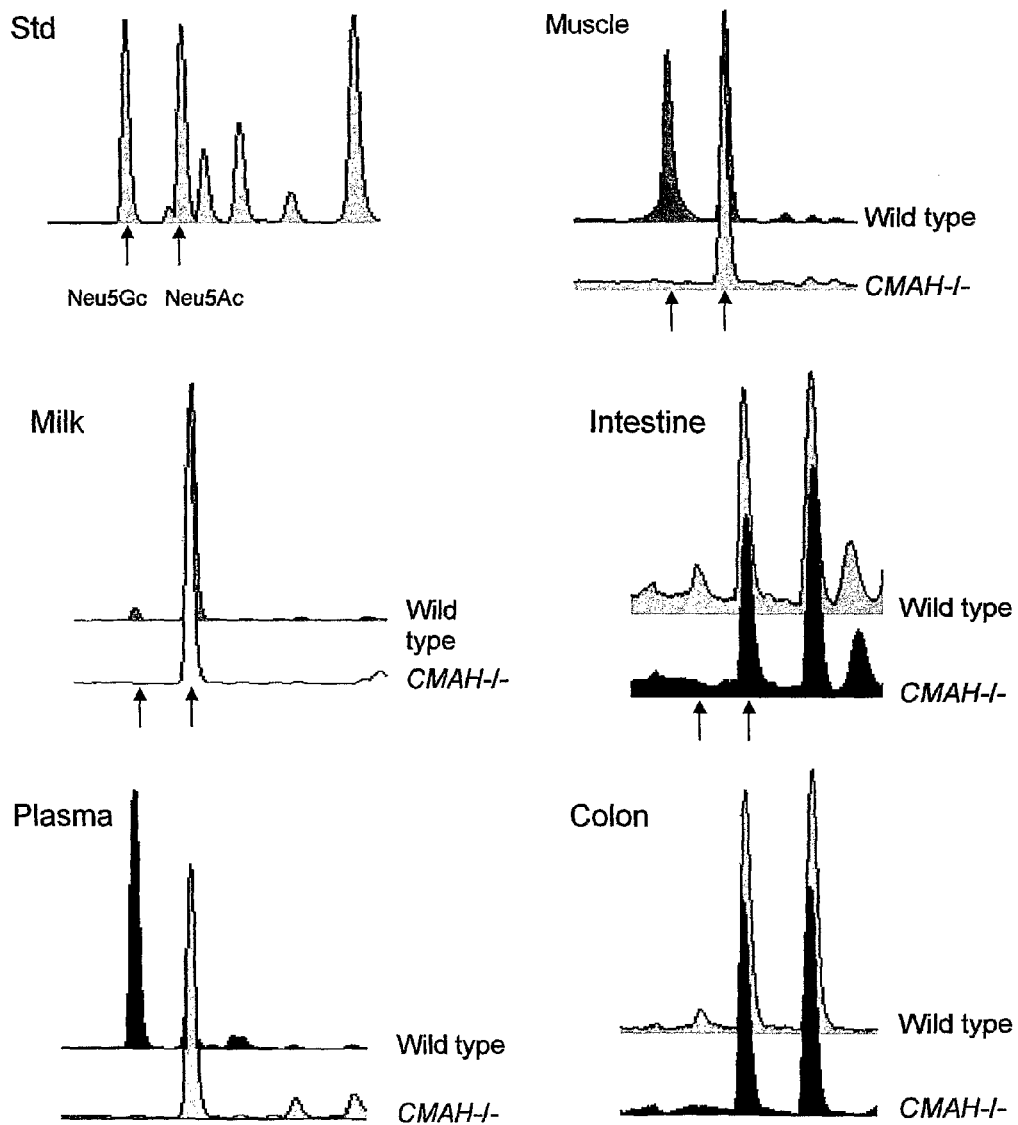
FIG. 15 depicts that CMAH null mice (Cmah−/−) are deficient in Neu5Gc expression in their tissues, milk and plasma. Immunohistochemistry of numerous CMAH null tissues using a chicken anti-Neu5Gc and a secondary horseradish peroxidase (HRP) conjugated anti-chicken antibody showed no appreciable staining (data not shown.) Sialic acids were released by 2M acetic acid and derivatized with DM) and analyzed by DMB-HPL). As shown, Neu5Gc was only found in tissues from wild type mice. The absence of Neu5Gc was confirmed using mass spectrometry (data not shown.)

CMAH null mice are deficient in Neu5Gc expression. To verify that CMAH null mice were deficient in CMAH expression, the mice were analyzed for Neu5Gc expression by immunohistochemistry using a chicken antibody specific for Neu5Gc, and biochemically, by derivatization with 1,2-diamino-4,5-methylene dioxybenzene (DMB) and HPLC analysis. Using the anti-Neu5Gc antibody, there was no staining in any tissues except for the mucinous secretions of the small intestine and colon. To confirm the lack of Neu5Gc in these tissues as well as those not stained positive, various tissues were homogenized and the sialic acids in glycopeptides and lipid extracts were released by acid and purified by ion exchange chromatography, derivatized with DMB and analyzed by HPLC (DMB-HPLC). No Neu5Gc was detectable in tissues staining negative with the anti-Neu5Gc antibody (data not shown), nor could we find evidence for presence of Neu5Gc in the intestine or the colon (FIG. 15). Thus, it is concluded that the staining of the mucin-rich regions of the intestine was non-specific. Furthermore, no Neu5Gc could be detected in the plasma or the milk of the CMAH null mouse (FIG. 15.)

The examples set forth above are provided to give those of ordinary skill in the art with a complete disclosure and description of how to make and use the preferred embodiments of the invention, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A viable and fertile transgenic mouse that
   a) comprises a genome having a homozygous mutation of the cytidine-5'-monophosphate N-acetyl neuraminic acid hydrolase (CMAH) gene,
   b) lacks expression of enzymatically active CMAH protein encoded by said CMAH gene, and
   c) lacks N-glycolylneuraminic acid (Neu5Gc) in one or more body fluid or tissue.

2. The mouse of claim 1, wherein said body fluid is selected from the group consisting of serum and milk.

3. The mouse of claim 1, wherein said tissue comprises muscle.

* * * * *

UNITED STATES PATENT AND TRADEMARK OFFICE
CERTIFICATE OF CORRECTION

| | |
|---|---|
| PATENT NO. | : 8,232,448 B2 |
| APPLICATION NO. | : 12/600378 |
| DATED | : July 31, 2012 |
| INVENTOR(S) | : Ajit Varki, Anna Maria Hedlund and Dzung Nguyen |

It is certified that error appears in the above-identified patent and that said Letters Patent is hereby corrected as shown below:

Col. 1, Line 4 Insert

--This invention was made with government support under R01-CA38701 awarded by the National Institutes of Health. The government has certain rights in the invention.--

Signed and Sealed this
Twenty-second Day of January, 2013

David J. Kappos
*Director of the United States Patent and Trademark Office*